US011851674B2

(12) United States Patent
Wolter et al.

(10) Patent No.: US 11,851,674 B2
(45) Date of Patent: Dec. 26, 2023

(54) THREE-DIMENSIONAL SCAFFOLD STRUCTURES WITH SELECTIVELY FUNCTIONALIZED POLYMER SYSTEMS, THEIR USE AND PROCESS FOR THEIR MANUFACTURE

(71) Applicant: Fraunhofer-Gesellschaft zur Foerderung der angewandten Forschung e.V., Munich (DE)

(72) Inventors: Herbert Wolter, Wuerzburg (DE); Somchith Nique, Wuerzburg (DE); Sebastian Hasselmann, Wuerzburg (DE); Caroline Kopittke, Wuerzburg (DE); Doris Heinrich, Wuerzburg (DE); Johannes Schwaiger, Wuerzburg (DE)

(73) Assignee: Fraunhofer-Gesllschaft zur Foerderung der angewandten Forschung e.V., Munich (DE)

( * ) Notice: Subject to any disclaimer, the term of this patent is extended or adjusted under 35 U.S.C. 154(b) by 815 days.

(21) Appl. No.: 16/683,954

(22) Filed: Nov. 14, 2019

(65) Prior Publication Data
US 2020/0149000 A1  May 14, 2020

(30) Foreign Application Priority Data
Nov. 14, 2018  (DE) .............. 102018128576

(51) Int. Cl.
*C08F 122/10* (2006.01)
*C12N 5/00* (2006.01)
*C08F 230/08* (2006.01)

(52) U.S. Cl.
CPC .......... *C12N 5/0068* (2013.01); *C08F 122/10* (2013.01); *C08F 230/085* (2020.02)

(58) Field of Classification Search
None
See application file for complete search history.

(56) References Cited

U.S. PATENT DOCUMENTS

| | | | | |
|---|---|---|---|---|
| 5,717,125 A * | 2/1998 | Wolter | .................... | C08G 77/22 |
| | | | | 556/427 |
| 6,106,606 A * | 8/2000 | Gellermann | ............. | C09D 7/68 |
| | | | | 427/213.3 |
| 6,106,696 A * | 8/2000 | Fecteau | .................. | C10G 35/12 |
| | | | | 208/65 |
| 6,124,491 A | 9/2000 | Wolter et al. | | |
| 8,748,647 B2 | 6/2014 | Wolter | | |
| 9,206,205 B2 * | 12/2015 | Wolter | ................. | C08G 77/392 |
| 9,233,992 B2 * | 1/2016 | Wolter | ................. | C07F 7/1804 |
| 9,532,931 B2 * | 1/2017 | Lübbe | .................... | A61K 6/896 |
| 9,631,113 B2 | 4/2017 | Rademacher et al. | | |
| 2007/0135572 A1 * | 6/2007 | Wolter | .................... | C08G 77/20 |
| | | | | 525/92 G |
| 2008/0317794 A1 * | 12/2008 | Gellermann | ............. | C09D 7/61 |
| | | | | 524/588 |
| 2011/0017944 A1 * | 1/2011 | Houbertz-Krauss | ..... | B01J 13/18 |
| | | | | 264/4.7 |
| 2014/0088279 A1 * | 3/2014 | Wolter | .................... | C08F 30/08 |
| | | | | 556/419 |
| 2014/0100349 A1 * | 4/2014 | Wolter | .................... | C08F 30/08 |
| | | | | 528/30 |
| 2014/0249325 A1 * | 9/2014 | Wolter | ................. | C08G 77/388 |
| | | | | 556/427 |
| 2014/0342100 A1 * | 11/2014 | Valeri | ..................... | G02B 1/12 |
| | | | | 522/170 |
| 2016/0185804 A1 * | 6/2016 | Wolter | .................... | C07F 7/081 |
| | | | | 556/427 |
| 2016/0340574 A1 * | 11/2016 | Vo | ............................ | C09K 8/80 |
| 2017/0313726 A1 * | 11/2017 | Wolter | ...................... | C07F 7/04 |
| 2018/0132986 A1 * | 5/2018 | Wolter | ............... | A61C 13/0835 |
| 2019/0275746 A1 * | 9/2019 | Huang | .................. | B29C 64/112 |
| 2021/0340492 A1 * | 11/2021 | Hasselmann | ........... | G03F 7/038 |

FOREIGN PATENT DOCUMENTS

| | | | | |
|---|---|---|---|---|
| DE | 10349766 A1 | 6/2005 | | |
| DE | 102017101823 A1 | 8/2018 | | |
| EP | 0682033 A2 | 11/1995 | | |
| EP | 2449616 B1 * | 8/2014 | .......... | C01B 3/0078 |
| EP | 2870209 B1 | 2/2018 | | |
| WO | WO-2018141657 A1 * | 8/2018 | ............. | B33Y 70/00 |

OTHER PUBLICATIONS

Inorganic polymer—Britannica Online Encyclopedia (2008) (Year: 2008).*
L. Alcock et al., 74 Tetrahedron, 1220-1228 (2018) (Year: 2018).*
B. Dhandayuthapani et al., International Journal of Polymer Science, 1-19 (2011) (Year: 2011).*
M. Jafari et al., J Biomed Mater Res Part B, 431-459 (2015) (Year: 2015).*
D. Loy, Hybrid Organic-Inorganic Materials, MRS Bulletin 364-367 (2001) (Year: 2001).*
Sima Rekstyte et al., "Direct Laser Fabrication of Composite Material 3D Microstructured Scaffolds", JLMN-Journal of Laser Micro/Nanoengineering vol. 9, No. 1, 2017, pp. 25-30.
Franziska Klein et al., "Two-Component Polymer Scaffolds for Controlled Three-Dimensional Cell Culture", Adv. Mater. 2011, pp. 1341-1345, 2011 WILEY-VCH Verlag Gmbh & Co. KGaA, Weinheim, www.MaterialsViews.com—www.advmat.de.
Benjamin Richter et al., "Guiding Cell Attachment in 3D Microscaffolds Selectively Functionalized With Two Distinct Adhesion Proteins", Adv. Mater. 2017, 29, 1604342 (6 pages), 2016 WILEY-VCH Verlag Gmbh & Co. KGaA, Weinheim, www.advmat.de—www.advancedsciencenews.com.

(Continued)

*Primary Examiner* — Alexander R Pagano
(74) *Attorney, Agent, or Firm* — Laurence A. Greenberg; Werner H. Stemer; Ralph E. Locher

(57) ABSTRACT

A three-dimensional scaffold structure and a process for its manufacture. The scaffold structure has a polymer system obtainable by photostructuring a starting material containing precursor molecules or inorganic polymers thereof having an organically polymerizable radical with at least one C=C double bond, an inorganically polymerizable silane-based radical and a functional group or derivative thereof.

13 Claims, 11 Drawing Sheets

(56) References Cited

OTHER PUBLICATIONS

Sabrina Schlie et al., "Three-Dimensional Cell Growth On Structures Fabricated From Ormocer® By Two-Photon Polymerization Technique", Article in Journal of Biomaterials Applications, vol. 22—Nov. 2007, pp. 275-287.

* cited by examiner

THREE-DIMENSIONAL SCAFFOLD STRUCTURES WITH SELECTIVELY FUNCTIONALIZED POLYMER SYSTEMS, THEIR USE AND PROCESS FOR THEIR MANUFACTURE

CROSS-REFERENCE TO RELATED APPLICATION

This application claims the priority, under 35 U.S.C. § 119, of German patent application DE 10 2018 128 576, filed Nov. 14, 2018; the prior application is herewith incorporated by reference in its entirety.

BACKGROUND OF THE INVENTION

Field of the Invention

The present invention pertains to a three-dimensional scaffold structure and a process for its manufacture. The scaffold structure comprises a polymer system obtainable by photo structuring a starting material containing precursor molecules or inorganic polymers thereof having an organically polymerizable radical with at least one C=C double bond, an inorganically polymerizable silane-based radical and a functional group or derivative thereof. The scaffold structure according to the invention can be used for interaction with biological cells.

In the field of cell culture, tissue engineering and lab-on-a-chip systems, scaffolds are needed to imitate the natural environment of biological cells and to control cell behavior such as proliferation, adhesion or differentiation. By varying the surface roughness, the structuring in the micrometer range or the chemical surface functionalization, it is possible, for example, to influence the behavior of biological cells.

There are numerous state-of-the-art materials that can be used as biological scaffold structures, e.g. hydro gels, glasses or fibres. In some cases, it is also possible to produce these using 3D printing, lithography or MPP processes. The polymerization process using multi-photon polymerization (MPP) or two-photon polymerization (2PP) is now used in many areas.

There are various material systems that are suitable for the TPA structuring of scaffold structures, but do not have a spatially selectively adapted surface chemistry. For example, ORMOCOMP® (multiple acrylate-ORMOCER®) was investigated as a possible TPA-structurable material for cell applications (Schlie S et al. (2007) Three-dimensional cell growth on structures fabricated from ORMOCER by two-photon polymerization technique. *Journal of biomaterials applications* 22:275-287).

In principle, there are two options for functionalizing polymer scaffold structures, namely, pre-polymerization functionalization (which corresponds to the approach used here) and post-polymerization functionalization. Examples for prepolymerization functionalizations of UV-reactive organic resins can be found for (meth)acrylates, e.g. with NHR and OH functionalities. Acrylic monomers containing OH can be found in EP 2 870 209 B1. However, no 3D scaffold structuring methods have been described for OH or NHR prefunctionalized polymers. In post-functionalization, various coatings (e.g. collagen) and functionalization methods (e.g. silanization, fluorination, photoinduced grafting, plasma treatments, adsorption or covalent binding of proteins and other bioactive molecules) as well as bulk modification (e.g. direct mixing with biofunctional molecules, carrier systems with micro- and nanoparticles) are possible. However, there is the problem that only the entire surface of the scaffold structure can be coated. A material is used that can be photostructured with high resolution and is then coated over in a further process step, thus functionalizing the entire surface.

Examples of selective functionalizations of polymer scaffold structures are known. In the literature, combinations of different material systems within a sample are described. The combination of TPA-structured PDMS, SZ2080, ORMOCLEAR®, PEG-DA within a sample is disclosed in (Rekstyte S (2014) Direct Laser Fabrication of Composite Material 3D Microstructured Scaffolds. *JLMN* 9:25-30). The combination of PEG and ORMOCOMP® within a sample is described in (Klein F et al. (2011) Two-component polymer scaffolds for controlled three-dimensional cell culture. *Advanced materials (Deerfield Beach, Fla.)* 23:1341-1345), where it was shown that the cells mainly adhere to ORMOCOMP® and thus cell adhesion and morphology can be controlled. However, the base material here is not identical, which can lead to very different process steps and thus to more complicated process procedures.

Several materials have already been combined within one sample and these materials have been functionalized with different biologically active groups on the surface in a further process step. Chemically, this was adjusted so that the different substances can only bind to one material and the samples show locally different surface chemistry and therefore the adhesion of the cells can be selectively influenced locally (Richter B et al. (2017) Guiding Cell Attachment in 3D Microscaffolds Selectively Functionalized with Two Distinct Adhesion Proteins). *Advanced materials (Deerfield Beach (Fla.)* 29). Since this is not an intrinsic functionalization, it is only present on the surface and must be realized by additional process steps.

SUMMARY OF THE INVENTION

The aim of tissue engineering is to control cell behavior, e.g. proliferation, adhesion, differentiation or migration, by means of external stimuli. The composition of the cell substrate plays a decisive role here. In order to simulate the natural cell environment in vitro, three-dimensional scaffolds should have defined properties such as surface chemistry, elasticity, roughness, topography and dimensionality. The chemical functionalization of the scaffold surface influences, among other things, the proliferation and adhesion ability of the cells. By using suitable chemical groups, it is also possible to control the binding of molecules from the cell medium that mediate cell adhesion. For more complex biological systems, selectively structured scaffold structures are necessary, which lead to an influence on the cell behavior due to locally varying properties, e.g. the modulus of elasticity, surface functionalization, surface polarity, fluorescence and surface roughness.

There is therefore a great need for a three-dimensional scaffold structure that can simulate a cell environment in vitro, can be selectively structured and has chemical functionalizations on the scaffold surface so that the cell behavior can be controlled in the desired way.

The problem underlying the invention was solved by providing the three-dimensional scaffold structure according to the invention. This structure comprises a polymer system which can be produced from precursor molecules having three functions, namely organic polymerizability by photostructuring, inorganic polymerizability by hydrolysis/condensation and bioactivity by functionalization or derivatization.

This invention concerns a 3D scaffold structure, the use of the 3D scaffold structure and a process for fabricating the 3D scaffold structure in accordance with the following points [1] to [15].

[1] A three-dimensional scaffold structure comprising a polymer system obtainable by photostructuring a starting material containing precursor molecules of formula (I) or inorganic polymers thereof:

Formula (I)

wherein the radicals and indices have the following meaning:
B is a straight-chain or branched or cyclic organic radical having at least one C=C double bond and 4 to 100 carbon atoms;
X is hydrogen, halogen, hydroxy, alkoxy, acyloxy, alkylcarbonyl, alkoxycarbonyl or $NR^4{}_2$;
R is alkyl, alkenyl, aryl, alkylaryl or arylalkyl;
$R^2$ is OH, COOH, $NR^4{}_2$, $NR^4{}_2H^+$ or SH or a derivative thereof;
$R^4$ is hydrogen, alkyl, aryl or alkylaryl;
$R^{Rg}$ is the backbone of a straight-chain or branched hydrocarbon bonded to the Si atom, where the backbone may be interrupted by heteroatoms or heteroatom-containing groups;
a=1, 2 or 3;
b=0, 1 or 2;
a+b=3;
c=1, 2, 3 or 4.

The three-dimensional scaffold structure according to point [1] preferably comprises scaffold structure parts made of a polymer system and fluid-filled open spaces between the scaffold structure parts with a minimum extent of 50 nm in each spatial direction, the polymer system being obtainable by treating a starting material with electromagnetic radiation, the starting material containing precursor molecules of the formula (I) or inorganic polymers thereof.

For example, the term "heteroatom" means —O—, —NH—, or —S—. The expression "heteroatom-containing groups" means, for example, those containing at least two heteroatoms and not more than one carbon atom, such as —O—CO—, —S—CO—, —NH—CO— and —CO—O—. For example, the hydrocarbon backbone may be interrupted by one or more members of the group consisting of —O—, —NH—, —S—, —O—CO—, —S—CO—, —NH—CO— and —CO—O—.

[2] The three-dimensional scaffold structure according to point [1], wherein the starting material contains precursor molecules of formula (II) or inorganic polymers thereof:

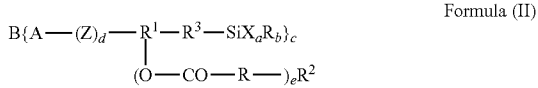

Formula (II)

in which the radicals and indices have the following meaning:
B, X, R, $R^2$, $R^4$, a, b, a+b and c have the same meaning as in formula (I);
$R^1$ and $R^3$ are independently of one another alkylene, arylene or alkylenearylene each having 1 to 20 carbon atoms, it being possible for these radicals to be interrupted by O, S, NR or NH,
A is O, S or NH for d=1 and Z=CO; or A is O, S, NH or COO for d=1;
Z is $CHR^4$; or A is O, S, NH or COO for d=0; and
e=0 or 1.

In point [2] it is preferred that the radicals and indices of the general formula (II) preferably have the following meaning: X is $(C_1-C_4)$alkoxy or halogen, R is $(C_1-C_4)$alkyl and $R^3$ is $(C_1-C_4)$alkylene.

A 3D scaffold structure according to point [2] is particularly preferred, wherein c is 1, d is 0, e is 0, $R^2$ is OH, X is $(C_1-C_4)$alkoxy or halogen, R is $(C_1-C_4)$alkyl, $R^3$ is $(C_1-C_4)$ alkylene and the organic radical BA is derived from acrylate or methacrylate.

[3] The three-dimensional scaffold structure according to point [1] or [2], said polymer system being derived from at least a first type of precursor molecules of formula (I) or (II), respectively, or inorganic polymers thereof, and from at least a second type of precursor molecules or inorganic polymers thereof, said second type differing from said first type at least or exclusively in that $R^2$ is hydrogen; or wherein the polymer system is derived from at least two kinds of precursor molecules or inorganic polymers thereof which differ at least or exclusively in the group $R^2$.

It is possible that the two species differ at least or exclusively in group $R^2$. The difference may be in the type of functionalization, i.e. whether $R^2$ is selected from OH, COOH, $NR^4{}_2$, $NR^4{}_2H^+$ or SH, and/or in the type of derivatization, i.e. which type of biofunctional molecule has been bound to $R^2$.

[4] The three-dimensional scaffold structure according to point [3], the difference being that $R^2$ is OH, COOH, $NR^4{}_2$, $NR^4{}_2H^+$ or SH in one type of precursor molecule and $R^2$ is a derivative of $R^2$ of the first type in the other type of precursor molecule.

[5] The three-dimensional scaffold structure according to one of the above points, wherein the derivative of $R^2$ is derived from a biofunctional molecule or from a spacer having a bound biofunctional molecule.

[6] The three-dimensional scaffold structure according to one of the above points, wherein the polymer system contains nanoparticles.

[7] The three-dimensional scaffold structure comprising two scaffold structure parts containing polymer systems described in one of the foregoing points, said polymer systems differing in at least one characteristic selected from the group consisting of the type of precursor molecule of formula (I) or (II), respectively, or an inorganic polymer thereof; the proportion of said precursor molecule of formula (I) or (II), respectively, or an inorganic polymer thereof in the total photostructurable compounds; the proportion of a precursor molecule corresponding, with the exception of $R^2$=H, to the precursor molecule used of formula (I) or (II), respectively; the content of nanoparticles; the proportion of the precursor molecule of formula (I) or (II), respectively, wherein $R^2$ is a derivative; and the nature of the derivative of $R^2$.

[8] The three-dimensional scaffold structure according to one of the above points, wherein the polymer systems are producible from a single type of precursor molecule, with the exception that the precursor molecules may differ in the presence and type of derivatization at $R^2$.

[9] The three-dimensional scaffold structure according to any one of points [1] to [7] comprising scaffold structure parts of a polymer system containing in the starting material first precursor molecules of formula (I) and (II), respectively, or inorganic polymers thereof, and scaffold structure parts of a polymer system containing in the starting material second precursor molecules of formula (I) and (II), respectively, or inorganic polymers thereof, different from the first precursor molecules.

[10] The three-dimensional scaffold structure according to one of the above points, comprising at least a first structural unit of a first thickness selected from the range of 10 µm to 100 mm and second structural units of a second thickness selected from the range of 100 nm to 1000 µm and branching off from the first structural unit, the second thickness at the branches being at most half the first thickness.

[11] The use of the three-dimensional scaffold structure according to one of the above points for interaction with biological cells in vitro.

[12] A method of producing a three-dimensional scaffold structure according to any one of points [1] to [11], comprising the following steps:
  (a) providing a photostructurable starting material described in point [1] or [2],
  (b) photostructuring the starting material of step (a) to form the 3D scaffold structure of any one of points [1] to [11]; and
  (c) removing the unreacted starting material.

[13] The method according to point [12], which comprises a first pass of steps (a) to (c) with a first position of photostructuring and a second pass of steps (a) to (c) with a second position of photostructuring different from the first position to form two partial structures of the three-dimensional scaffold structure.

The position of the second photostructuring is preferably chosen in such a way that the two partial structures are covalently connected by the photostructuring. The positions of the two photostructures are therefore preferably adjacent to each other. The two substructures can belong to the same or different hierarchy levels. The type of functional group $R^2$ is selected from OH, COOH, $NR^4_2$, $NR^4_2H^+$ or SH, wherein $R^4$ is hydrogen, alkyl, aryl or alkylaryl. The derivative is obtainable by reacting the group $R^2$ with a biofunctional molecule mentioned in the present description or a spacer-modified derivative thereof.

[14] The method according to point [13], wherein the starting materials of the first pass differ from those of the second pass in at least one characteristic selected from the group consisting of
  the type of precursor molecule of formula (I) or (II), respectively, or an inorganic polymer thereof;
  the proportion of the precursor molecule of formula (I) or (II) or an inorganic polymer thereof in the total photostructurable compounds;
  the proportion of a precursor molecule which, with the exception of $R^2$=H, corresponds to the precursor molecule of the formula (I) or (II) used;
  the content of nanoparticles;
  the proportion of the precursor molecule of formula (I) or (II), respectively, wherein $R^2$ is a derivative; and
  of the nature of the derivative to $R^2$.
Here the difference in "proportion" also includes the possibility that the ingredient concerned is contained in the source material of one pass and not contained at all in the other.

In a preferred form, the precursor molecules or the inorganic polymers differ in the two passes in the type of functional group $R^2$ or in the derivative of group $R^2$ or in both.

[15] The method according to point [13] or [14] using only a single type of precursor molecule of formula (I) or (II), respectively, or an inorganic polymer thereof, except that the precursor molecules may differ in the presence and type of derivatization at $R^2$, and wherein said type is the same or different in both passes.

By using only a single type of precursor molecule of formula (I) or (II) in both passes, the process can be simplified, while at the same time the different concentrations and derivatizations of the precursor molecules, the sequence of the process steps, the shape and dimensions of the substructures and the presence of nano-molecules offer great possibilities for variation in terms of structures and properties.

Advantages of the Invention

The functionalization and/or derivatization of the precursor molecules leads to the fact that the desired groups can be uniformly incorporated into the 3D scaffold structure according to the invention and can thus be present throughout a structural part, namely both at the surface and in the inside of the structural part.

By means of intrinsic functionalization, high-resolution macroscopic scaffold structures can be produced in conjunction with different functionalization variants with the same basic chemical structure.

The developed organically functionalized inorganic polymer systems are biocompatible, intrinsically functionalized and photostructurable with all common methods. By combining these methods, it is possible to produce any 3D-formed scaffold structures in the centimeter range with a structuring resolution down to the submicrometer range. Through intrinsic functionalization, scaffold structures with locally varied functionalization can be produced through several successive structuring steps.

Furthermore, it is possible to covalently bind certain bioactive substances such as proteins or similar to the functional groups in a further process step (e.g. biotin-avidin coupling). Due to the selective structuring, these substances can be spatially varied.

The addition of nanoparticles makes it possible to achieve an additional intrinsic surface roughness in the nanometer range without a further process step. This can be varied at will by the diameter of the nanoparticles and adapted to each cell type or the desired cell behavior.

By the affinity of different cells for certain environmental properties, selective scaffold structures therefore allow the targeted control of cell migration and colonisation behavior in different areas of the scaffold structure.

The combination of biocompatibility, photostructurability and, in particular, intrinsic functionalization, which can be adjusted to a high degree of variability, enables the production of high-resolution cell scaffolds with locally adjustable chemical and physical properties. This enables, for example, targeted influence on stem cell differentiation.

The invention-based 3D scaffold structure can be used, for example, for the differentiation or sorting of different systems, for the development of body-on-a-chip systems or for the production of artificial organs with several cell types.

The accuracy of the structural parts can be increased by a hierarchical structure of the 3D scaffold structure. At the same time, a higher concentration of nanoparticles can be used while maintaining the accuracy of the structure.

The hierarchical structure allows systems to be provided that are very stable on the one hand and have a high inner surface on the other. In addition, the combination of different structuring methods makes it possible to produce samples much more efficiently in terms of time and cost.

Other features which are considered as characteristic for the invention are set forth in the appended claims.

Although the invention is illustrated and described herein as embodied in three-dimensional scaffold structures with selectively functionalized polymer systems, their use and process for their manufacture, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 8, parts B and C are histograms of the contact events of cells with the columnar surfaces as a function of the area of contact for (B) hydroxy-functionalized and (C) amine-functionalized columns.

DETAILED DESCRIPTION OF THE INVENTION

Three-Dimensional Scaffold Structure

Figure 1:
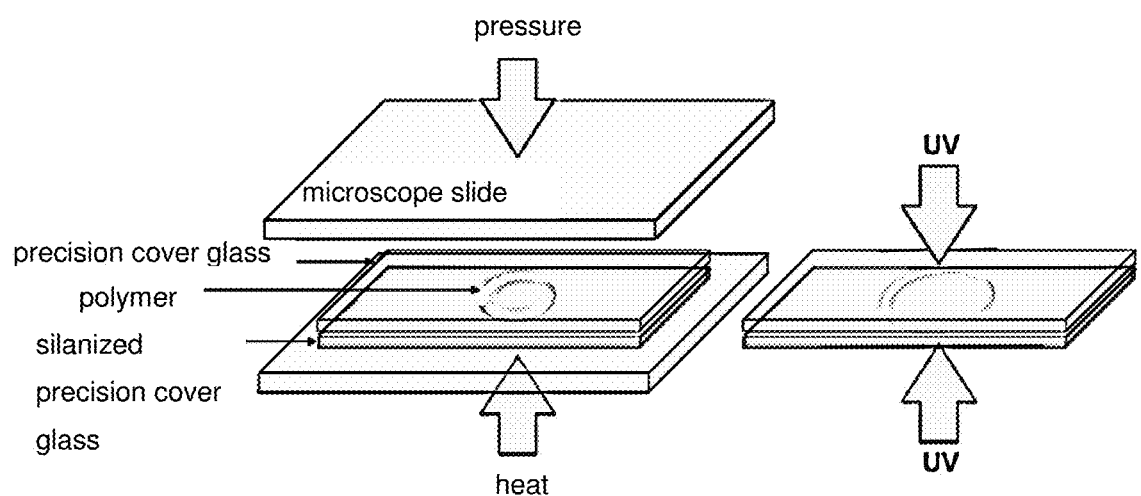
FIG. 1 shows the production of thin smooth hybrid polymer layers. A prepolymer drop is pressed between two precision microscope cover glasses to form a thin layer (left) and then cured with UV radiation (right). After the cross-linking step, the non-silanized cover glass can be removed, leaving a thin smooth polymer layer on the silanized cover glass.

In the context of this invention, the inventive "three-dimensional scaffold structure", which can also be referred to simply as the "3D scaffold structure" below, means a three-dimensional solid structure which preferably comprises scaffold structural parts made of a polymer system and fluid-filled open spaces between the scaffold structural parts. The scaffold structural parts are solid. The fluid is a substance that is gaseous or liquid at room temperature. These fluid-filled spaces are cavities or intermediate spaces (in particular in the case of quasi-three-dimensional structures). The fluid-filled spaces are not closed, but open to the surface of the scaffold structure and are thus open pores in the scaffold structure. That is, the fluid and other substances can move between the fluid-filled spaces and the environment of the scaffolding structure. As a result, the fluid-filled spaces and thus the substituents $R^2$ of the polymer system are accessible to substances from the environment of the scaffold structure. Preferably, the scaffold structure is designed such that the fluid-filled spaces are accessible to those substances which are to interact with the substituent $R^2$ of the polymer system. For example, when $R^2$ is an enzyme, the scaffold structure is designed such that the fluid-filled spaces are accessible to a substrate of the enzyme. The fluid is preferably a liquid medium, for example a cell culture medium. The structured polymer is preferably cross-linked and represents the scaffold structural parts of the 3D scaffold structure. The minimum thickness of the scaffold structure parts is determined by the resolution of the photostructuring. This resolution can be up to 10 nm, so that the minimum dimension of the scaffold structure parts in each spatial direction is at least 10 nm. For example, the minimum dimension is 10 nm to 10 mm, preferably 1 µm to 1000 µm. The fluid-filled spaces between the scaffold structure parts have a minimum dimension of 50 nm, preferably 100 nm, more preferably 1000 µm in each direction; a range of 1 µm to 1000 µm being preferred and a range of 1 µm to 50 µm being more preferred. A combination of scaffold structure parts with a minimum dimension of 1 to 1000 µm in each spatial direction and fluid-filled spaces with a minimum dimension of 1 to 50 µm in each spatial direction is preferred.

The scaffold structure according to the invention is preferably designed such that, after being filled with water as a fluid, it can consist of at least 50 percent by volume of water at room temperature.

In the context of this invention, "three-dimensional" means the spatial extension of a one-piece structure into all three spatial coordinates. The expansion can be essentially uniform in these three directions, so that, for example, a cylindrical shape, a columnar, cuboid or cubic matrix structure is present. However, it is also possible, for example, that the expansion in two directions is larger, but only small in the third direction, so that the three-dimensional structure has a planar effect, e.g. a membrane or layer. Such a surface form is preferred for the individual structural units, i.e. they have a length x, a width y and a thickness z, where x and y are each at least twice as large as z, preferably at least three times as large and more preferably at least five times as large.

In addition to the one-piece spatial structures, the term "three-dimensional structures" also includes structural parts that are adjacent to one another but arranged without direct contact with one another. The resulting overall structure is also referred to as the "quasi-three-dimensional" scaffold structure. Unless otherwise indicated, the term "three-dimensional" shall include the term 'quasi-three-dimensional'.

In the context of this invention, the term "biocompatible" means that the scaffold structure and other components, e.g. nanoparticles that may be contained, do not cause any toxic, apoptotic, undesirable immunological or other undesirable reaction for the cells or tissue, both in terms of their material composition and in terms of their structure, and that they do not disturb or hardly disturb cellular and molecular processes, even after possible internalisation of nanoparticles or degradation of nanoparticles and/or scaffold structure.

The 3D scaffold structure can simulate a wide range of tissues, from soft tissue (0.4 to 350 MPa) such as brain and connective tissue to hard tissue (10 to 1500 MPa) such as cartilage and bone.

The structure can be used for the interaction, e.g. adhesion, of cells. A scaffold structure within the scaffold of the present invention is, in particular in its preferred form, a structure which not only allows cells to adhere or adhere to the surface, but also in particular allows cells to grow into or integrate into the scaffold structure itself.

Photostructurability

The starting material used for the fabrication of the 3D scaffold structure according to the invention can be photostructured. The term "photostructurable" used here means that the material in question can be polymerised by treatment with electromagnetic radiation. The electromagnetic radiation can, for example, be formed by a focused light or by a laser beam.

Examples of photostructuring processes are rapid prototyping, 3D printing, lithography and MPP.

Precursor Molecules and Inorganic Polymers Thereof

The 3D scaffold structures or the present invention are based on organically functionalized inorganic polymer structures. They are mainly based on $\equiv$Si—O—Si$\equiv$ and may be modified with heteroelements. As usual, the inorganic polymer structure can be built up from precursor silanes (see formula (I) or (II)) as part of the sol-gel process.

The precursor molecules are silanes and the inorganic polymers derived therefrom are silicic acid poly(partial) condensates which are constructed using structural elements which have a partially or completely hydrolysable/hydrolysed and/or condensable/condensed silane radical. In addition, these condensates may contain foreign metal atoms that can be condensed into such systems, such as boron, aluminum, germanium, tin, titanium or zirconium. Silica poly (partial)condensates containing foreign metals are then heterosilicic acid poly(partial)condensates.

In this application, the term "precursor molecules or inorganic polymers thereof" includes these silanes and silicic acid poly(partial)condensates and heterosilicic acid poly (partial)condensates derived therefrom. The term "precursor molecules or inorganic polymers thereof" includes the possibility that both precursor molecules and inorganic polymers thereof are present.

The organically polymerizable molecule part B, which can contain one or more double bonds and is linked to the silane fraction, can be used to build up an additive organic network. The connection unit is organic in nature and variable in length, structure and composition.

The silanes of the formula (I) or (II) can be hydrolysed via the X radicals. An inorganic network containing $\equiv$Si—O—Si$\equiv$ can be built up via the hydrolysable groups by hydrolysis and condensation.

All parts of the molecule can contribute to the modification of properties. The variability leading to special property combinations is given by the introduced additional functionality $R^2$ in variable number and/or with variable portion and variable distance from the molecule core.

Examples of precursor molecules carry acrylate and/or methacrylate groups as organically polymerizable molecule parts B.

If the term "(meth)acrylic" is used here, then this term stands both for "methacrylic" and for "acrylic". In the context of polymers, this means that the polymer contains or is obtained from methacrylic functional monomers, acrylic functional monomers or both.

Non-hydroxy precursor molecules are for example ($C_{1-8}$ alkyl)acrylates and ($C_{1-8}$ alkyl)methacrylates, in particular ($C_{1-4}$ alkyl)acrylates and ($C_{1-4}$ alkyl)methacrylates such as methyl, ethyl, propyl and butyl (meth)acrylates. For example, methacrylates such as methyl methacrylate and butyl methacrylate are used as precursor molecules. The precursor molecules carrying hydroxy groups preferably contain exactly one hydroxy group per monomer. The hydroxy groups may be primary or secondary hydroxy groups. For example, the precursor molecules carrying hydroxy groups are hydroxyalkyl (meth)acrylates, such as hydroxy ($C_{1-4}$alkyl) acrylates and/or hydroxy ($C_{1-4}$alkyl) methacrylates. Further examples are hydroxy($C_{1-4}$alkyl) acrylates such as hydroxyethyl acrylate (HEA) or hydroxybutylacrylate (HBA).

In the present application, a hydrocarbon group designated by the prefix 'alk', for example in alkyl, alkenyl, alkynyl or aralkyl, may be a straight-chain or branched or cyclic group, unless otherwise indicated.

The alkyl radicals in formula (I) or (II), for example, are straight-chain, branched or cyclic radicals having 1 to 20, in particular having 1 to 10 carbon atoms, and preferably lower alkyl radicals having 1 to 6, in particular preferably having 1 to 4 carbon atoms. Special examples are methyl, ethyl, n-propyl, i-propyl, n-butyl, i-butyl, s-butyl, t-butyl, n-pentyl, n-hexyl, cyclohexyl, 2-ethylhexyl, dodecyl and octadecyl.

The alkenyl radicals in formula (I) or (II) are, for example, straight-chain, branched or cyclic radicals having 2 to 20, preferably 2 to 10 carbon atoms, and preferably lower alkenyl radicals having 2 to 6 carbon atoms, such as vinyl, allyl and 2-butenyl.

Preferred aryl radicals are phenyl, biphenyl and naphthyl. The alkoxy, acyloxy, alkylamino, dialkylamino, alkylcarbonyl, alkoxycarbonyl, arylalkyl, alkylaryl, alkylene and alkylenearylene radicals are preferably derived from the alkyl and aryl radicals mentioned above. Special examples are methoxy, ethoxy, n- and i-propoxy, n-, i-, s- and t-butoxy, monomethylamino, monoethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The said radicals may optionally bear one or more substituents, e.g. halogen, alkyl, hydroxyalkyl, alkoxy, aryl, aryloxy, alkylcarbonyl, alkoxycarbonyl, furfuryl, tetrahydrofurfuryl, amino, monoalkylamino, dialkylamino, trialkylammonium, amido, hydroxy, formyl, carboxy, mercapto, cyano, isocyanato, nitro, epoxy, $SO_3H$ or $PO_4H_2$.

Among the halogens, fluorine, chlorine and bromine and especially chlorine are preferred.

For a≤2 or b=2, the radicals X and R can each have the same meaning or a different meaning.

The radical B is derived from a substituted or unsubstituted compound $B(AH)_c$ having at least one C=C double bond, such as vinyl, allyl, acrylic and/or methacrylic groups, and 4 to 100, preferably 6 to 50, carbon atoms. Preferably, B is derived from a substituted or unsubstituted compound having two or more acrylate or methacrylate groups. Such compounds are referred to in the following as (meth)acrylates. If the compound $B(AH)_c$ is substituted, the substituents may be selected from the above substituents. The -AH group can be —OH, —SH, —NHR, —$NH_2$ or —COOH and c can have values from 1 to 4.

Via its free valencies, the radical B is each linked to a group -$A(Z)_d$- which may have the following forms:
—O—CO—, —S—CO—, —NH—CO—, —O—$CH_2$—, —O—CHR—, —S—$CH_2$—, —S—CHR—, —NH—$CH_2$—, —NH—CHR—, —CO—O—$CH_2$—, —CO—O—CHR—, —O—, —S—, —NH— and —CO—O—, where R=alkyl, aryl or alkylaryl. The alkyl radicals are straight-chain, branched or cyclic radicals having 1 to 20, in particular 1 to 10 carbon atoms, and preferably lower alkyl radicals having 1 to 6, in particular 1 to 4 carbon atoms. Special examples are methyl, ethyl, n-propyl, i-propyl, n-butyl, i-butyl, s-butyl, t-butyl, n-pentyl, n-hexyl, cyclohexyl, 2-ethylhexyl, dodecyl and octadecyl. Preferred aryl radicals are phenyl, biphenyl and naphthyl.

A group "COO" mentioned in the present invention may be part of both an acyloxy group (—O—(C=O)—R) and an alkyloxycarbonyl group (—(C=O)—O—R).

The silanes used in this invention can be produced as described in European published patent application EP 0 682 033 A2.

In the presence of two or more C=C double bonds in the remainder B, the formation of a three-dimensional organic network is possible. The distance between the Si atom and the remainder B, i.e. the chain length, and the presence of other functional groups in this chain can influence the mechanical properties (e.g. flexibility) and the physicochemical properties (adsorption, refractive index or adhesion) of the poly(hetero)condensates.

In the silanes used in accordance with the invention, the radicals and indices of the general formula (I) or (II) preferably have the following meaning:
X=($C_1$-$C_4$)-alkoxy, preferably methoxy and ethoxy, or halogen, preferably chlorine;
R=($C_1$-$C_4$)-alkyl, preferably methyl and ethyl;
$R^3$=($C_1$-$C_4$)-alkylene, preferably methylene, ethylene and propylene;
the other radicals and indices having the same meanings as defined above for formula (I) and (II), respectively.

Preferably, B in the general formula (I) or (II) represents a substituted or unsubstituted organic radical having one or more acrylate and/or methacrylate groups. For example, B in formula (I) or (II) is derived from acrylic acid esters of trimethylolpropane, pentaerythritol, dipentaerythritol, $C_2$-$C_4$-alkanediols, polyethylene glycols, polypropylene glycols or, optionally substituted and/or alkoxylated, bisphenol A.

Functionalization and Derivatization

The inventive 3D scaffolding structure is functionalized, i.e. it has functional groups. These functional groups are referred to herein as functionalizations and are represented in formula (I) or (II) by $R^2$. $R^2$ is OH, COOH, $NR^4_2$, $NR^4_2H^+$ or SH or a derivative thereof, wherein $R^4$ is hydrogen, alkyl, aryl or alkylaryl.

The inventive 3D scaffold structure is optionally derivatized. The derivative is a condensation derivative of $R^2$, i.e. a derivative which can be obtained by condensation reaction of $R^2$ with another compound. Specifically, the derivative is obtainable by reacting group $R^2$ with a biofunctional molecule or spacer-modified biofunctional molecule, as defined below. Derivatisation may take place before or preferably after photostructuring.

In —$NR^4_2H^+$, the restriction may be that $R^4$ is not H, except in isolated, non-"Michael-active" C=C. Likewise, in an embodiment —SH is only present in isolated, not "Michael-active" C=C.

In the case of amino functionalizations, care must be taken to ensure that the activity is retained after photostructuring. It may therefore be necessary to protect the amines with Br-t-BoC, for example.

By means of derivatization, a compound having a desired biological function or effect can be covalently bound to the group $R^2$. It is therefore generally referred to in this invention as a "biofunctional molecule".

Instead of the biofunctional molecules mentioned in the context of this invention, dyes can also be bound as derivatives, so that the description related to biofunctional molecules applies equally to dyes. For example, Alexa 647 (Alexa 647 Hydrazid, Life Technologies GmbH, Darmstadt, Germany) can be used as a dye and bonded to the surface of a carboxy-functionalized hybrid polymer. The dye preferably has a molecular weight of less than 5000, more preferably less than 2000.

According to claim 1, $R^2$ is the group OH, COOH, $NR^4{}_2$, $NR^4{}_2H^+$ or SH or a derivative thereof. Derivatization results in $OR^5$, $COOR^5$, $NR^4R^5$, $NR^4R^5H^+$ or $SR^5$, where $R^5$ is the remainder of the biofunctional molecule or dye.

This biofunctional molecule may be bound to $R^2$ directly or by means of a spacer and/or bifunctional coupling molecule described below.

Thus, a derivative comprises a compound which is a condensate of $R^2$ and biofunctional molecule or of $R^2$, spacer and biofunctional molecule, wherein a bifunctional coupling molecule may be interposed in each case.

Examples of biofunctional molecules that can be bound to the 3D scaffold structure via the functional group $R^2$ are amino acids, peptides, proteins, enzymes, nucleic acids, nucleotides, oligonucleotides, Polynucleotides, DNA, RNA, carbohydrates, monosaccharides, disaccharides, oligosaccharides, polysaccharides, polymers such as PEG, antibodies or fragments thereof, collagen, fibronectin, hyaluronic acid, integrins, and cell receptors. Preferred is the group consisting of peptides, oligonucleotides and oligosaccharides and the group consisting of proteins, polynucleotides and polysaccharides. The inventive 3D scaffolding structure may contain one or more of the above connections.

Biofunctional molecules can also be components that surround a cell in vivo as a microenvironment. Thus, the inventive 3D scaffold structure can simulate such a microenvironment. A microenvironment consists mainly of the extracellular matrix (ECM), growth factors and cytokines. The extracellular matrix contains fibre proteins, adhesion proteins and carbohydrates. The fibre proteins can be selected from collagen, fibrillin or elastin. The carbohydrates can be selected from glycosaminoglycans, proteoglycans, hyaluronic acid, heparan sulphate, dermatan sulphate, chondroitin sulphate and keratan sulphate. The adhesion proteins can be selected from laminins, vitronectin and fibronectin. Components of the basement membrane can be selected from laminins, entactin and proteoglycans. Further components are cell receptors such as the integrin family, peptides and hydrogels such as alginate or PEG. The inventive 3D scaffold structure may contain one or more or all of the above components of the microenvironment of a cell.

A preferred derivative of $R^2$ contains at least one member of the group consisting of an amino acid or an oligomer or polymer thereof, a nucleotide or oligomer or polymer thereof, a saccharide or oligomer or polymer thereof, a dye and PEG. An oligomer mentioned in this application contains at least two monomers.

A particularly preferred derivative of $R^2$ contains at least one member of the group consisting of peptides, oligonucleotides, oligosaccharides, proteins, polynucleotides, polysaccharides, dyes and PEG.

Derivatizations of $R^2$ are possible with the functional groups of the biofunctional molecules by the formation of the following bonds:
  OH can form an ester or ether bond, respectively, with COOH or OH of a biofunctional molecule;
  COOH can form an ester or amide bond, respectively, with OH or $NH_2$ of a biofunctional molecule;
  $NR^4{}_2$ or $NR^4{}_2H^+$ can form an amide bond with COOH of a biofunctional molecule;
  SH can form a thioester bond, ether bond or thioether bond, respectively, with COOH, OH or SH of a biofunctional molecule.

These biofunctional molecules can be bound directly or via the spacers described below to the group $R^2$ of the scaffold structure. If a spacer is used, it may contain at one end one of the functional groups as mentioned above for the biofunctional molecules, creating the said bond between the scaffold structure and the spacer. At the other end, the spacer may contain one of the functional groups as defined above for $R^2$ to form one of the above-mentioned bonds.

A possibility of coupling biofunctional molecules or dyes or, optionally, intermediate spacers exists through the use of bifunctional coupling molecules which selectively bind to functional groups and in turn couple these to primary amino groups carrying the desired substance. Examples of such coupling molecules are 1-ethyl-3-(3-dimethylaminopropyl) carbodiimide hydrochloride (EDC, Life Technologies GmbH, Darmstadt, Germany) and N-hydroxysulfosuccinimide (Sulfo-NHS, Life Technologies GmbH, Darmstadt, Germany).

With respect to $R^2$ in formula (I) or formula (II), the inventive 3D scaffold structure may have the following three combinations (i) to (iii), either in the same scaffold structure part or in different scaffold structure parts:
  H and non-derivatized $R^2$
  (ii) H and non-derivatized $R^2$ and derivatized $R^2$
  (iii) non-derivatized $R^2$ and derivatized $R^2$.

In addition to the covalent binding of the biofunctional molecule described above, either directly or indirectly via a spacer to $R^2$, the biofunctional molecule can also be bound non-covalently to $R^2$ with the functionality OH, COOH, $NR^4{}_2$, $NR^4{}_2H^+$ or SH or a spacer having this functionality, for example via hydrogen bonding, ionic interaction or complexation.

Hierarchical Structure of the 3D Scaffolding Structure

In this invention, 3D scaffolding structures or structural parts of different size ranges can be formed. For example, structures are produced in the millimeter, micrometer, submicrometer or nanometer range. The specification of a size value of a structure means that free spaces, pores or cavities are created in the structure which have the dimensions of the specified value at least in one spatial direction, i.e. in length, width or depth. Preferably a structure with pores is created whose dimensions correspond to this size value. If, for example, a structure in the range of 1 to 100 µm is formed, this means that pores of a size of about 1 to 100 µm are formed. The same applies to the other specifications of size values for structures used here. The 3D scaffolding structures can have a hierarchical structure and, for example, have the following three hierarchy levels:
  Level 1: a superstructure of a size from 10 µm to 100 mm, preferably 100 µm to 50 mm, more preferably 500 µm to 5 mm;
  Level 2: a fine structure of size 100 nm to 1000 µm, preferably 1000 nm to 100 µm, more preferably 5 µm to 50 µm;
  Level 3: Nanoparticles of size 1 to 1000 nm, preferably 5 to 800 nm, more preferably 10 to 500 nm.

In any case, the respective superstructure has such large free spaces or pores that a large number of desired fine structures can be formed in it. And in any case, the respective fine structure has such large free spaces or pores that it can contain a large number of nanoparticles. The term "large number" means at least 5, preferably 10 to 500. In other words, the "large number" requires that the structure has a dimension in at least one spatial direction, preferably at least two spatial directions, i.e. in the length, width or depth direction, which is greater than the mean size of the nanoparticles by a factor of 5 to 1000.

In the inventive 3D scaffolding structure, the hierarchical structure can be defined by at least two hierarchy levels. A structural unit (I) represents the superior hierarchy level, structural unit (II) follows as the next hierarchy level, and structural unit (III) represents the lowest of the three levels. The number of hierarchy levels is of course not limited to three. The additional surface produced by the nanoparticles represents a further hierarchical level.

In the embodiment (A1) having at least two hierarchical levels, the 3D scaffold structure according to the invention contains at least one structural unit (I) of a thickness (i) selected from the range from 10 µm to 100 mm and structural units (II) branching off from the structural unit (I) of a thickness (ii) selected in each case from the range from 100 nm to 1000 µm, the thickness (ii) at the branches being at most half the thickness (i).

In the embodiment (A2) having at least three hierarchy levels, the 3D skeleton structure according to the invention contains at least one structural unit (I) of a thickness (i) selected from the range from 100 µm to 100 mm, structural units (II) branching off from the structural unit (I) and of a thickness (ii) respectively selected from the range from 10 µm to 1000 µm, and structural units (III) branching off from the structural units (II) and of a thickness (iii) respectively selected from the range from 100 nm to 100 µm, wherein at the branches of the structural units (II) from the structural unit (I) the thickness (ii) is at most half the thickness (i) and at the branches of the structural units (III) from the structural units (II) the thickness (iii) is at most half the thickness (ii).

The structural units (I), (II) and (III) can be produced using the same or different structuring processes. Basically, any known structuring procedure can be employed for each structure hierarchy level.

For example, superstructures in the centimeter range can be realized by rapid prototyping or 3D printing, structures in the millimeter to micrometer range by lithography and structures in the submicrometer range by MPP.

Nanoparticles

In one embodiment of the present invention, the 3D scaffold structure may contain nanoparticles.

The average diameter of all nanoparticles is always smaller than the average thickness of the scaffold structure. All nanoparticles are preferably predominantly or completely embedded in the scaffold structure in one embodiment. The ratio of the dimensions of nanoparticles to the thickness of the scaffold structure is preferably less than 1:1, preferably 1:10 or less, more preferably 1:100 or less.

Preferably the nanoparticles are contained in a high proportion in the scaffold structure. Preferred are volume proportions from 1 to 60%, more preferred 5 to 30% or weight proportions from 1 to 50%, more preferred 5 to 40%. The volume and weight percentages given here refer to the dry weight of all components.

The polymerisation of the scaffold material binds the nanoparticles to the resulting scaffold, resulting in a crosslinked polymer with nanoparticles bonded to it. Since nanoparticles are also bound at the interface of strongly and weakly crosslinked polymers, a number of nanoparticles protrude at least partially from the structure.

The invented 3D scaffold structure may contain nanoparticles of inorganic substances such as gold or other precious metals or metals or metal oxides, calcium phosphate and calcium hydrogen phosphate or other mixed phosphates, silicon-based oxidic materials such as silicates, silicon oxides such as silicon dioxide. The nanoparticles can also be DynaBeads. The inventive 3D scaffold structure may contain nanoparticles of organic materials, especially organic polymers. The organic polymers can be selected from polylactides (PLA), poly(lactid-co-glycolid)en (PLGA), polycaprolactones (PCL), polyglycolides, di- and tri-block polymers, for example, PCL/PGA di-block systems, polyorthoesters (POE), polyanhydrides, polyhydroxyalkanoates (PHA), polypyrroles (PPy), polypropylene carbonate, polyethylene carbonate, polyalkylcyanonitrile and polyethylene glycol.

The invention-based 3D scaffold structure can contain one or more of the nanoparticles of inorganic substances and/or nanoparticles of organic materials mentioned above.

The nanoparticles can lead to an increased surface roughness. In this invention, the surface roughness is determined by atomic force microscopy and given as a value $Z_z$ in nanometers. Preferred values of $Z_z$ are 10 to 1000 nm, preferably 100 to 800 nm. Alternatively, the surface roughness can be specified as value Zq. Preferred values of Zq are 1 to 1000 nm, even more preferred 50 to 100 nm. The surface roughness is determined by the size and number or volume fraction of the nanoparticles in the structure. The preferred combination of medium size nanoparticles and volume fraction of nanoparticles in the structure is 5 to 1000 nm at 3 to 50%, more preferably 30 to 800 nm at 10 to 40%. In the case of larger nanoparticles, the volume fraction is lower, so that it is preferred that the product of the numerical value in nanometers of the mean size of the nanoparticles and the numerical value in percent of the volume fraction of the nanoparticles in the structure is in the range from 500 to 15000.

In this invention, the surface roughness is determined according to ISO4287.

With regard to the high surface roughness, the nanoparticles and the photostructurable material can be selected in such a way that the refractive indices differ only slightly. Thus, a high accuracy of the photo structuring is possible. By adjusting the refractive indices, it is possible to use a high concentration of nanoparticles and still achieve a high accuracy of photostructuring.

When hollow particles are used within a biodegradable matrix, cell behavior can be specifically influenced by the use of nutrients, growth factors or other active substances. The active ingredient is gradually released during the degradation of the matrix.

The nanoparticles and/or the structural materials can be functionalised and connected via linking groups for stronger and targeted binding of the nanoparticles to the scaffold structure. These relationship groups can be used as spacers. If these spacers are of different lengths, the effective surface area of the structure can be further increased. In one embodiment, the incorporation of nanoparticles into the structure and the linkage with nanoparticles can be combined with spacers of different lengths by means of functionalization. The binding of the nanoparticles can take place via the functional group $R^2$ in formula (I) or (II) or via another functionalization. By binding the nanoparticles to a part of the precursor molecule of formula (I) or (II), the content of nanoparticles can be adjusted.

The surface of the nanoparticles can be chemically functionalized to create a suitable chemical interface for the cells or to covalently bind the nanoparticles to the matrix material via corresponding photocrosslinkable groups (e.g. 3-(trimethoxysilyl)propylmethacrylate). The surface of the nanoparticles can also be functionalized with bioactive materials or molecules as they are named above as examples of biofunctional molecules.

In addition, the nanoparticles can be mesoporous and filled with appropriate active substances, drugs, nutrient solutions or similar (drug-delivery principle).

The reactive group of a nanoparticle can form a covalent bond with the reactive group of a biofunctional molecule. The nanoparticle thus has on its surface a first functional group 1A covalently linked to a functional group 2A of the biofunctional molecule, wherein the functional group 1A is a different group than the functional group 2A. The two binding groups 1A and 2A must be complementary, i.e. able to form a covalent bond with each other. The same groups 1A and 2A as below can be used for binding the biofunctional molecule to the spacer.

The nanoparticles may contain nutrients, messenger substances, cell receptors or other substances which may be released into a medium with a delay as an alternative to or in addition to the surface functionalization mentioned above. The nanoparticles may contain one or more of these substances selected from growth factors, cytokines, cell adhesion proteins, dyes such as fluorescent amines, chemokines, vitamins, minerals, fats, proteins, nutrients, fibre-forming proteins, carbohydrates, adhesion proteins, cell receptors, pharmaceuticals, DNA, RNA, aptamers, angiogenic factors, lectins, antibodies, antibody fragments, peptides, hydrogels or inhibitors.

The nanoparticles may contain stabilizers selected from carbohydrates such as trehalose, proteins, polyethylene glycols or detergents.

In one form, the nanoparticles may contain one or more of the biofunctional molecules described above as components of the microenvironment of cells.

These biofunctional molecules may be directly covalently bound to the 3D scaffold structure and/or covalently bound to the nanoparticles and/or non-covalently embedded in the nanoparticles as derivatizations of $R^2$.

Spacers

A biofunctional molecule can be bound to the $R^2$ group via a spacer.

The spacer can be attached before or preferably after photo structuring.

The spacer is at least bifunctional, i.e. it has a reactive group which is reacted with the group $R^2$ of the 3D scaffold structure according to the invention, preferably in a condensation reaction, and it has a reactive group which is reacted with a reactive group of the biofunctional molecule, preferably in a condensation reaction. Preferably both reactive groups react in a condensation reaction.

The two reactive groups of the spacer can be the same or different.

If they are different, the reactive group of the spacer to be converted with the biofunctional molecule can also be a first functional group 1A, which can form an affine, preferably covalent, bond with a complementary group 2A of a biofunctional molecule. The first functional group 1A may be selected from the group consisting of amino group, carboxy group, epoxy group, maleimido group, alkyl ketone group, aldehyde group, hydrazine group, hydrazide group, thiol group and thioester group. The functional group 2A of the active ingredient may be selected from the group consisting of amino group, carboxy group, epoxy group, maleimido group, alkyl ketone group, aldehyde group, hydrazine group, hydrazide group, thiol group and thioester group. Thus, a spacer has on its surface a first functional group 1A covalently linked to a functional group 2A of the biofunctional molecule, wherein the functional group 1A is a group different from functional group 2A. The two binding groups 1A and 2A must be complementary, i.e. able to form a covalent bond with each other.

The spacer preferably has a hydrocarbon chain optionally interrupted by oxygen atoms and/or amino groups with a chain length of preferably 5 to 10,000 atoms.

For example, if $R^2$ is a carboxylic acid group, the spacer may be attached to the 3D scaffold structure via amino groups. In particular, the spacer may be an at least difunctional amine of optionally different length such as polyethylene glycol $NH_2$ and/or a polyalkylene amine such as tetraethylene pentamine.

In this context, the terms "derived from polyalkylene glycol-$NH_2$", "derived from polyethylene glycol-$NH_2$", "derived from polyalkylene amine" and "derived from tetraethylene pentaamine" shall mean that a polyalkylene glycol/polyethylene glycol modified terminally with $NH_2$ groups, or an oligoalkylenamine/tetraethylenepentamine is used, so that the resulting spacer has at least two coupling groups, one of these groups being used to bind the 3D scaffold structure according to the invention and the other of these groups being used to bind the biofunctional molecule. The bond is usually designed as a —C(O)NH coupling group.

The spacer preferably comprises both spacers derived from polyethylene glycol-$NH_2$ of different lengths and spacers derived from tetraethylene pentamine.

By selecting the group $R^2$ of the scaffold structure, the groups at both ends of the spacer and the reactive group of the biofunctional molecule, a 3D scaffold structure/spacer/biofunctional molecule linkage can be obtained by forming the bonds described above for derivatization.

The binding of the biofunctional molecule takes place, for example, by reacting a carboxy group of the biofunctional molecule, e.g. the C-terminal end of a peptide, with an amino group of the spacer. This implementation creates amide groups.

Preferably, the spacer is also tied to the 3D scaffold structure according to the invention via amide groups. This conversion can be carried out e.g. by means of a state of the art process using a carbodiimide compound as catalyst.

In one embodiment, any existing free functional groups of the 3D scaffold structure and/or spacer are blocked.

The covalent bond is obtainable for example between the spacer and the biofunctional molecule by reacting a carboxyl group of the biofunctional molecule with an amino group of the spacer or by reacting an amino group acidified by azidoacetyl chloride with a DNA or RNA molecule.

The presence of a surface spacer of variable length as described above, in particular of different length, increases the mobility of the biofunctional molecule and thereby improves the reaction kinetics with other compounds.

The spacer preferably has amino groups at each end. One of these groups is used for binding to the 3D scaffold structure, the other for covalent binding to the biofunctional molecule. This makes it possible to bind biofunctional molecules in an inexpensive and common way.

By using spacers of different lengths, the number of biofunctional molecules per unit area or unit volume can be significantly increased so that the desired biofunction can be enhanced.

The inventive 3D scaffold structure can be modified with the spacer before the biofunctional molecule is attached.

The free amino end of the functionalization of PEG-$NH_2$ or TEPA is suitable for binding to a biofunctional molecule.

Proteins can be attached to COOH groups of the 3D scaffold structure via covalent bonds. Since proteins are made up of amino acids, they possess both free —COOH and free —$NH_2$ groups. Therefore, both carboxy and amine residues on the 3D scaffold structure are possible as binding terminals to the protein to form an amide bond.

A tetraethylene pentamine (TEPA) of the formula $H_2N$—$CH_2CH_2$—$NH$—$CH_2CH_2$—$NH$—$CH_2CH_2$—$NH$—$CH_2CH_2$—$NH_2$ may be a mixture of several compounds (oligomers) which are formed from a different monomer number and therefore have a different chain length. The TEPA used in the present connection can therefore, for example contain one or more of the compounds selected from the group consisting of N-(2-aminoethyl)-N'-{2-{2-aminoethyl)amino}ethyl}-1,2-ethanediamine; 4-(2-aminoethyl)-N-(2-aminoethyl)-N'-{2-{(2-aminoethyl)-amino}ethyl}-1,2-ethanediamine; 1-(2-aminoethyl)-4-[(2-aminoethyl)amino]ethyl]piperazine) and 1-[2-[[2-[(2-aminoethyl)amino]ethyl]amino]ethyl]piperazine). These compounds differ in their structure and thus in their reactivity with the reaction partners, i.e. the invented 3D scaffold structure on the one hand and the biofunctional molecule on the other. Thus, the term "tetraethylenepentamine" or "TEPA" used here includes not only the compound of the above formula but also any of the other compounds mentioned above alone or in a mixture of two or more of these compounds.

The polyethylene glycol-$NH_2$ (PEG-$NH_2$) used in this invention is derived from polyethylene glycol (PEG). PEG is a polymer of ethylene glycol monomer units and can have different chain lengths. Typical chain lengths of purchasable PEGs include 200, 400 or 600 monomer units. In the present invention, the PEG-$NH_2$ may preferably consist of 5 to 600 monomer units. PEG-$NH_2$ of a single chain length or PEG-$NH_2$ of different chain lengths can be used. This means that the present invention also includes an embodiment in which a mixture of PEG-$NH_2$ of different chain lengths is used. In addition, this mixture may also contain one or more of the abovementioned different TEPAs.

In this way, spacers of different length and reactivity can be obtained on the 3D scaffold structure according to the invention. The use of spacers of different lengths has the advantage that the sensory surface can be increased. In concrete terms, this means that the biofunctional molecules can be present on the 3D scaffold structure in several layers and still be easily accessible.

In an embodiment of the present invention, the $NH_2$ terms of the $R^2$ groups can be acidified with azidoacetyl chloride. This functionalization allows click chemistry to be used as a binding mechanism between the 3D scaffold structure and the biofunctional molecule. Using click chemistry, a wide variety of molecules can be bound to the 3D scaffold structure. This can be done without the addition of additional reaction chemistry.

Use of the 3D Scaffold Structure According to the Invention

The inventive 3D scaffold structure can be used for interaction with biological cells in vitro or in vivo.

For medical use in or on the human or animal body, the present invention concerns a 3D scaffold structure for medical, therapeutic or diagnostic use. This use is based on the interaction with biological cells.

When used for 3D cell cultures, photostructurable ORMOCER®s enable high-resolution 3D cell scaffold structures that are precisely adapted to the needs of different cell types. By suitable topographies (dimensionality, curvature, pore size, roughness), as well as chemical and physical material properties realistic, but precisely controllable growth conditions can be created.

When using 3D scaffold structures for implants, the choice of suitable surface and material properties improves the biocompatibility of implants. Spatially varying Scaffold properties can promote the colonization of different cell types at different sites of the implant and thus support its correct functioning and integration in the body.

When used for diagnostic methods (cell sorting, lab-on-a-chip), the affinity of the invented 3D scaffold structures for different functionalizations can be used to separate different cell types from each other (e.g. healthy and pathogenic) by stimulating them to migrate in different directions. In addition, a site-selective adhesion of certain cell types is possible. In combination with high-resolution microstructuring, this is of particular interest for lab-on-a-chip applications.

When using 3D scaffold structures for tissue engineering, different cell types have to be made to colonise different parts of the scaffold structures in order to grow complex tissues in the laboratory and to perform their function there in interaction with other cells. These areas can be independently adjusted to the desired cell type and its intended function in a selective scaffold of different materials.

Process for the Fabrication of the 3D Scaffold Structure According to the Invention:

Stereolithography offers a possibility for the fabrication of finely structured scaffolds or highly complex structures. In this technique, a chemical reaction, namely photopolymerization, is initiated by electromagnetic radiation. The material to be structured or the material formulation to be structured must therefore fulfil the requirement of being able to react with light. As a result, a phase transition from liquid to solid takes place in the exposed areas. In the subsequent development step, only the remaining liquid material is dissolved away. With the help of a laser beam, structures can be generated layer by layer. The advantages of this method are that highly organized three-dimensional scaffold structures with defined porosity, pore size and interconnectivity of the pores can be produced with high reproducibility and this is possible with only a few process steps.

A special case of stereolithography, namely two-photon polymerization (2PP), offers good resolution. With this technique ultrafine structures can be generated at high resolution. It is based on the simultaneous absorption of two photons (two photon absorption, TPA), which triggers the decay of the initiator molecules and thus the subsequent chemical reaction between the generated radicals and the monomers. Due to the simultaneous absorption of two photons, very high light intensities are required for excitation, which can be realized by ultrashort laser pulses. The rate of two-photon absorption depends non-linearly on the intensity.

As a result, polymerization takes place only in a spatially narrow area around the laser focus within the liquid to be solidified, whereby resolutions of <100 nm can also be achieved. If the focus is moved through the material, three-dimensional microstructures are created in the exposed areas in one process step. This allows a relatively small space within the liquid to be solidified to be controlled with relatively good accuracy, which is solidified by the input energy. The production of the moulded body can therefore take place within a corresponding liquid, no longer (only) on its surface.

In a preferred embodiment of the invention, the liquid is solidified by irradiation with femtosecond laser pulses. Common polymerizable materials can be exposed to ultrashort laser pulses with high peak energy, e.g. Ti:sapphire femtosecond laser pulses. These are irradiated with wavelengths in the range of about 800 nm into the resins to be solidified.

Ti sapphire lasers can preferably be used as suitable lasers (either with the fundamental wavelength of 780 nm or, depending on the absorption behavior of the liquid to be cured, with the second harmonic at 390 nm); other NIR lasers (e.g. with emitted wavelengths of 800 nm to about 1500 nm) are also suitable. But other laser irradiation is also possible if the light source used can irradiate the liquid with an intensity suitable for multiphoton excitation. This property is offered in particular by short pulse lasers with moderate average power. The material to be cured must be transparent for the laser wavelength used. If, for example, the material to be solidified could be polymerised with one photon at 390 nm, any wavelength of 400 nm or more could be used for two- or multi-photon polymerisation; depending on the resin, 500-1000 nm are the most suitable due to the transparency conditions. If longer wavelengths are used, polymerization can also be initialized by n-photon absorption, where n is greater than 2.

In particular, the use of femtosecond lasers as radiation sources results in bodies/layers with high lithographic resolution. The type and duration of irradiation also allow the degree of crosslinking to be varied so that different physical properties (e.g. degradability at different rates, adjustable modulus of elasticity) can be achieved with one and the same material if required. The degree of cross-linking can also be varied within a scaffold structure. This can either be done at certain points or as a gradient. With this process not only three-dimensional structures on substrates (carrier materials) can be produced, but also three-dimensional self-supporting bodies can be produced completely out of the volume.

The inventive process makes it possible to produce three-dimensional shaped bodies with a continuous porous network within the shaped body over a large area by light-induced cross-linking processes, in particular by multi-photon absorption technology over a wide wavelength range using a wide variety of laser and optical systems in-situ. In particular, the process described can be used to produce large structures and shaped bodies with a size down to the cm range.

By combining different photostructuring methods, desired hierarchical structures can be created. In this way, a hierarchical structure from the centimetre to the nanometre range can be adapted at will. For example, superstructures in the centimetre range can be produced by a rapid prototyping process and substructures by multi-photon absorption (MPA).

The pore structures are selected as desired, e.g. depending on the cell types to be applied to the carrier matrix.

In contrast to stereolithographic methods, which solidify an object layer by layer in a bath of a liquid solidifiable by the action of radiation while moving the object further into the bath, a three-dimensional body to be produced by means of femtosecond laser irradiation is produced in only one working step on a surface or in volume.

The two- or multi-photon polymerization of the organic residue polymerizable by two-photon or multi-photon polymerization can take place via one or more groups that can be polymerized radically. Non-aromatic C=C double bonds such as allyl or vinyl groups are suitable as radical polymerizable groups, but double bonds accessible to Michael addition are particularly preferred.

Examples of photostructurable matrix materials are inorganically condensable silanes and their condensates and/or polymers. These silanes contain one or more substituents or groups bonded to the silicon via oxygen and having ester bonds or, if desired, also having ether and/or thioether bonds, as well as organically polymerizable units such as C=C double bonds or ring-opening systems, e.g. epoxy groups. The silanes can be condensed inorganically and/or polymerized organically via the C=C double bonds. Such an organic polymerization can, for example, be carried out with the aid of 2-photon polymerization (2PP), so that structured, essentially monomer-free materials can be obtained. By varying the proportion of inorganically cross-linkable units and/or organically polymerizable units, the mechanical properties of the hybrid polymers produced from the silanes can be specifically adjusted to resemble those of natural, soft or hard tissue. These hybrid polymers are particularly suitable for the fabrication of scaffold structures.

The well-known ORMOCER® hybrid materials can be solidified both by organic polymerization of C=C double bonds and by inorganic crosslinking reactions (Si—O—Si bridge formation), whereby the presence of organically polymerizable C=C double bonds permits spatial structuring during polymerization.

A desired three-dimensional matrix structure is produced in an embodiment of the invention.

In a first step of the process to produce a desired structure, data are provided that describe the desired structural structure. The data describes the geometric shape of the structure.

In a further step of the process, a precursor of a biopolymer is provided. The precursor is a starting material in the sense of a precursor of the biopolymer, for example in the form of a monomer. The biopolymer is, for example, a biocompatible and/or biodegradable polymer.

The precursor is locally irradiated with electromagnetic radiation, whereby the irradiation, in particular the selection of the areas to be irradiated, is carried out according to the structural structure described by the data. This means that exactly those coherent subsets of the plane or space are irradiated which are defined by the data. The electromagnetic radiation can, for example, be formed by a focused light or by a laser beam.

In accordance with the invention, the electromagnetic radiation is measured in such a way that in the irradiated regions of the precursor a two- or multiphoton absorption takes place, by means of which the precursor in the irradiated regions is polymerized to the biopolymer, so that it at least partially solidifies there. Since the irradiation of the precursor is locally targeted according to the structural structure described by the data, the polymer formed is formed with the desired structure.

In another embodiment of the process, parts of the precursor that are not polymerized after irradiation are washed out. Cavities, among other things, are emptied by the rinsing out.

The procedure for fabricating the 3D scaffold structure according to the invention comprises the following steps:
  (a) providing photopolymerizable monomers having a functionalization,
  (b) photostructuring the monomers provided in step (a) to form a 3D scaffold structure,
  (c) removing the remaining monomers.

The following aspects (i) to (iv) are also important in the process according to the invention, whereby (i) the composition of the monomers in step (a), (ii) the repetition of steps (a) to (c), (iii) the derivatization of the functionalization and (iv) the sequence of the process steps concern:
  (i)
Steps (a) to (c) can be used to produce polymers in which each polymer chain has one or more types of functionalization. For example, if a homopolymer is produced from a monomer having a functionalization, the homopolymer contains only one type of functionalization. For example, if a copolymer is prepared from a monomer with one functionalization and a monomer with another functionalization, the copolymer has two different types of functionalization. For example, if a copolymer is prepared from a monomer with functionalization and a monomer without functionalization, i.e. $R^2$=H in formula (I) or (II), the copolymer has a lower degree of functionalization. For example, by using mixtures of monomers, oligomers or prepolymers of different composition, polymers can be obtained which have the desired functionalizations in the desired number and in the desired polymer chain ranges.

A further example is conceivable with the functionalization $R^2$=SH. By varying index c, the ratio of C=C double bonds to $R^2$=SH can be set as desired. When a thiol-en polymerization is carried out, the SH groups can be used in excess of the C=C double bonds, so that finally non-reacted SH groups remain.

(ii)

Steps (a) to (c) can be repeated using other monomers, whereby 3D scaffold structures with a functionalization in one scaffold structural part and a structurally or numerically different functionalization in another scaffold structural part can be specifically preserved. In the present invention, the minimum dimension of a scaffold structure part in each spatial direction corresponds to the resolution in photostructuring, namely 100 nm, with a minimum dimension of 1 μm being preferred.

(iii)

The functionalized monomers can be reacted with other compounds and thus derivatized. For example, a hydroxy functionalization with a carboxylic acid can be converted into an ester. A molecule of any function can be attached to this carboxylic acid, for example a group with biological affinity or function. The derivatization of the hydroxy group can already take place on the monomer, so that the derivative is uniformly incorporated into the 3D scaffold structure according to the invention and is thus present throughout, namely on the surface and inside, in a structural part. Derivatisation can also be carried out after structuring has taken place or after partial structuring has taken place (see aspect (ii) above). This allows desired groups to be introduced, whereby these groups mainly bind to the functionalizations on the surfaces of the 3D scaffold structure or the surfaces of the 3D scaffold structure parts and less to the functionalizations in closer meshed interior of the structure. In this way, 3D scaffold structures can be specifically created in which the functionalities on the surface differ qualitatively or quantitatively from the functionalities inside the structured element.

(iv)

The following basic processes can be used to produce the 3D scaffold structure from a starting material containing a precursor molecule: (1) inorganic polymerization (hydrolysis and condensation) of the precursor molecule; (2) derivatization of $R^2$; (3) photostructuring. These procedures can be performed in the alternative sequences 1-2-3, 2-1-3, 1-3-2.

If an additional procedure (4) of introducing a spacer is carried out, the alternative sequences 1-4-2-3, 4-2-1-3, 1-4-3-2, 1-4-3-2, 4-1-2-3, 4-1-3-2 are possible.

By a targeted combination of (i) to (iv), 3D scaffold structures can be obtained in which structural parts are contained which independently of one another have one or more desired types of functionalization, wherein additionally in each structural part a functionalization derivative can be present either continuously or mainly on the surface. Thus, the type, number, location, spatial distribution and functionalizations as well as their derivatizations and their mobility and distances from the functionalizations can be specifically and as required adjusted in the 3D scaffold structure according to the invention.

The combination of (i) to (iv) and the targeted incorporation of nanoparticles into desired scaffold structural parts, starting from a single species of a precursor molecule of the formula (I) or (II), makes it possible to obtain a multiplicity of different structures and functionalities and combinations thereof in one and the same 3D scaffold structure according to the invention.

The influence of topographic and chemical substrate properties on cell migration behavior can be investigated in several steps. In a single step, the topography of the cell substrate can be varied from two-dimensional, flat layers to quasi-three-dimensional column fields and three-dimensional cubic lattice structures. In another step, the effect of the functionalized polymer systems can be investigated. In a further step, the findings of the first steps are combined to form three-dimensional structures of mixed functionalization.

EXAMPLES

I. Synthesis Example 1

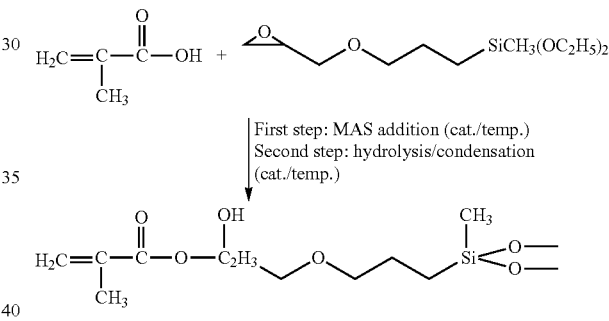

The synthesis of the resin system with $R^2$=OH is described in DE 4416857. Triphenylphosphine as catalyst, BHT as stabiliser and 142.1 g of methacrylic acid are added to 372.6 g of 3-glycidyloxypropylmethyldiethoxysilane in a dry atmosphere and stirred at 85° C. The product is then subjected to a heat treatment process. After addition of ethyl acetate as solvent and $H_2O$ for hydrolysis with HCl as catalyst, stirring at 30° C. is carried out. The processing is carried out after several days of stirring by repeated shaking with aqueous NaOH and with water and filtration. It is first rotated off and then drawn off with an oil pump vacuum. The result is a liquid resin with a viscosity of approx. 3-5 Pa·s at 25° C.

The resin system with $R^2$=—OH can be used as a general basic structure for further functionalization to e.g. $R^2$=—$CO_2H$, —$NR_2$.

II. Synthesis Example 2

(a) Synthesis of the resin system is performed with $R^2$=OH/$CO_2H$ in a molar ratio of 0.5:0.5. The solution of 20.0 g (76 mmol) of the resin system from Synthesis Example 1 and 3.8 g (38 mmol) succinic anhydride in 15 ml THF is heated under reflux. One acid group of the anhydride forms an ester bond with the OH group, the remaining acid group of the anhydride then represents the desired $CO_2H$ group. After the complete turnover the processing takes place (removal of THF, dissolving in ethyl acetate, extraction with $H_2O$, removal of volatile components). The result is a liquid resin.

(b) Synthesis of the resin system with $R^2=OH/CO_2H$ in a molar ratio of 1.0:0.8 (ratio of the starting material; in the finished product, the ratio is 1.0:0.76 according to NMR analysis). The solution of 20.8 g (0.08 mol) of the resin system of Synthesis Example 1 and 6.4 g (0.04 mol) of succinic anhydride in 10 ml of THF and after addition of 1,8-diazabicyclo [5.4.0] undec-7-ene (=DBU) (0.01 mol DBU/mol succinic anhydride) is heated to reflux. After the complete turnover the processing takes place (removal of the THF, dissolution in ethyl acetate, extraction with $H_2O$, removal of the volatile components). The result is a liquid resin.

III. Synthesis Example 3

Synthesis Stage 1
According to the description in DE 103.49766.8

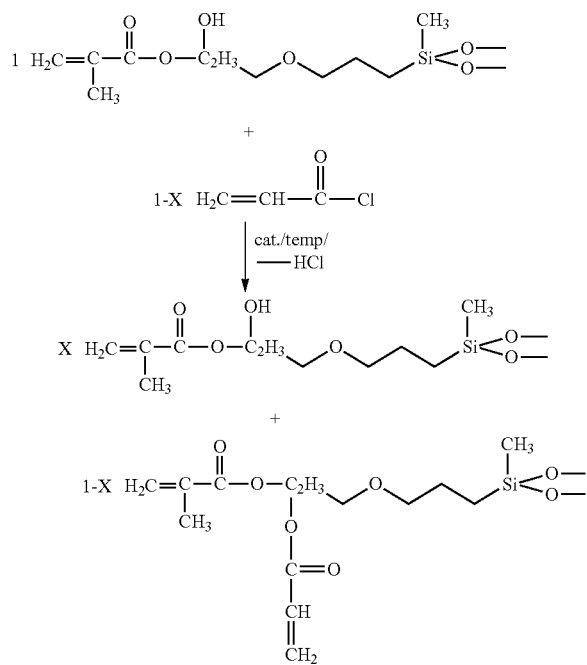

Base resin A (X≈0.61)
11.72 g (0.130 mol) acrylic acid chloride is added to 78.15 g (0.30 mol) of the resin system from Synthesis Example 1 and 16.70 g triethylamine in 300 ml THF as solvent under dry atmosphere and cooling by ice bath with stirring and stirring is continued at room temperature. After the usual processing to separate the amine hydrochloride and acidic by-products produced during the addition and to remove the volatile components with an oil pump vacuum, a liquid resin is obtained.

Synthesis Stage 2
Synthesis of the resin system with $R^2$=OH/NEt$_2$ is carried out in a molar ratio of approximately 0.63:0.37. The amount of diethylamine (0.5 g) corresponding to the acrylate content is added to 4.37 g of base resin system A while stirring and continuing stirring at room temperature until complete addition. The —CH=CH$_2$ double bonds of the acrylate are partially converted with diethylamine to —CH$_2$—CH$_2$—NEt$_2$. After removing the volatile components with an oil pump vacuum, a liquid resin is obtained.

The above examples show that the —OH group of the compound from example 1 can be used for further functionalization with —CO$_2$H groups and the (meth)acrylic group for proportional functionalization with —NR$^3{}_2$ groups ($R^3$=—C$_2$H5).

Functionalization with —CO$_2$H groups can be carried out according to Synthesis Example 2 in such a way that —OH groups remain in addition to the —CO$_2$H groups, i.e. a system containing —CO$_2$H and —OH groups is obtained, whereby different proportions are possible.

The proportional functionalization with —NR$^3{}_2$ groups takes place according to Synthesis Example 3 in such a way that besides the —NR$^3{}_2$ groups there are also —OH groups, i.e. a system containing —NR$^3{}_2$ and —OH groups, whereby different proportions are possible.

Thus, liquid resin systems or final cured systems with defined macroscopic scaffold structure in connection with different functionalization variants are possible with the same basic chemical structure.

Application Examples

In the Application Examples, the hybrid polymer systems shown in Table 1 were used, which were intrinsically functionalized by different chemical groups (—OH or —COOH/—OH or —N(C$_2$H$_5$)$_2$/—OH).

TABLE 1

| Degrees of functionalization of the hybrid polymers used in the application example | |
|---|---|
| Functionalization $R^2$ | Degree of functionalization |
| Hydroxy (—OH) | 100% |
| Carboxy (—COOH/—OH) | 50%/50% |
| Amine/hydroxy (N(C$_2$H$_5$)$_2$/—OH) | 39%/61% |

Application Example 1: Dye Binding

N-hydroxysulfosuccinimide (Sulfo-NHS, Life Technologies GmbH, Darmstadt, Germany) was used to bind the dye Alexa 647 (Alexa 647 Hydrazid, Life Technologies GmbH, Darmstadt, Germany) to the surface of carboxy-functionalized hybrid polymer.

For this purpose, 30 μm thick layers of the carboxy-functionalized hybrid polymer were doctored onto a cover glass. As a reference, an identical layer was produced from a purely hydroxy-functionalized hybrid polymer, which cannot be bonded via the coupling molecule.

Parts of these samples were treated using a chemical coupling process that selectively binds to carboxy groups to attach the dye Alexa 647. The following procedure for dye binding was performed on both samples. To activate the carboxy group, 0.4 mg EDC and 1.1 mg Sulfo-NHS were dissolved in 1 mL MES buffer (0.1 M MES, 0.5M NaCl, pH 6.0), 200 mL of this solution were pipetted onto the sample and reacted for 30 min at room temperature. The sample was then rinsed several times with PBS solution and the Alexa647 dye solution (0.1 mg in 500 μl PBS) was pipetted on. After two hours, the reaction with hydroxylamine-HCL (Life Technologies GmbH, Darmstadt, Germany) was suppressed, the sample was rinsed with PBS and placed in it overnight to dissolve unreacted substances. For comparison, parts of these samples were not treated with this method.

Confocal 3D fluorescence images were recorded on both samples (Leica TCS, SP8X, Leica Microsystems GmbH, Wetzlar, Germany). In each case, the transition of the polymer to the uncoated cover glass was examined in order to clarify the effect of the bonding by means of fluorescence. Each sample was examined both at the treated site and at an untreated site. Only at the treated site of the carboxy-functionalized sample a strong fluorescence of Alexa 647 could be detected. At their untreated sites and during both measurements on the hydroxy-functionalized sample, only the very weak autofluorescence of the polymer and interfacial scattering could be detected.

This study shows, on the one hand, that the carboxy groups of intrinsic functionalization are chemically accessible on the surface and, on the other hand, that they can be used to bind site-selectively dyes, proteins or other bioactive substances in a simple way.

Application Example 2: Cell Migration Measurements

Cell migration measurements were carried out on layers of two hybrid polymer systems intrinsically functionalised by different chemical groups (—OH or —N$(C_2H_5)_2$/—OH) (see Table 1). These were compared with cell migration measurements on borosilicate glass cover glasses, which is a widely used reference surface. The same measurements were performed in column structures from the two polymer systems, as well as in column structures where some columns consist of the polymer —OH and others of the polymer —N$(C_2H_5)_2$/—OH.

2 wt. % UV initiator (Irgacure® 369, Ciba Geigy, 2-benzyl-2-dimethylamino-1-(4-morpholinophenyl)-butanon-1) was added to the prepolymer to obtain a photocrosslinkable or photostructurable material. Precision microscope cover glasses (borosilicate glass, No. 1.5H, A. Hartenstein, Germany) were used as the substrate for the layers. Their surface was silanized with 3-(trimethoxysilyl)propylmethacrylate (Sigma-Aldrich Chemie GmbH, Germany) to increase adhesion. The uncrosslinked prepolymer was then dripped on and covered with another cover glass and compressed at a temperature of 50° C. with a weight of 4 kg for 20 minutes. The prepolymer between the cover glasses was then cured by UV radiation (10 min, BK 850, Beltran®) and the unsilanized cover glass was removed (see FIG. 1).

Figure 2:
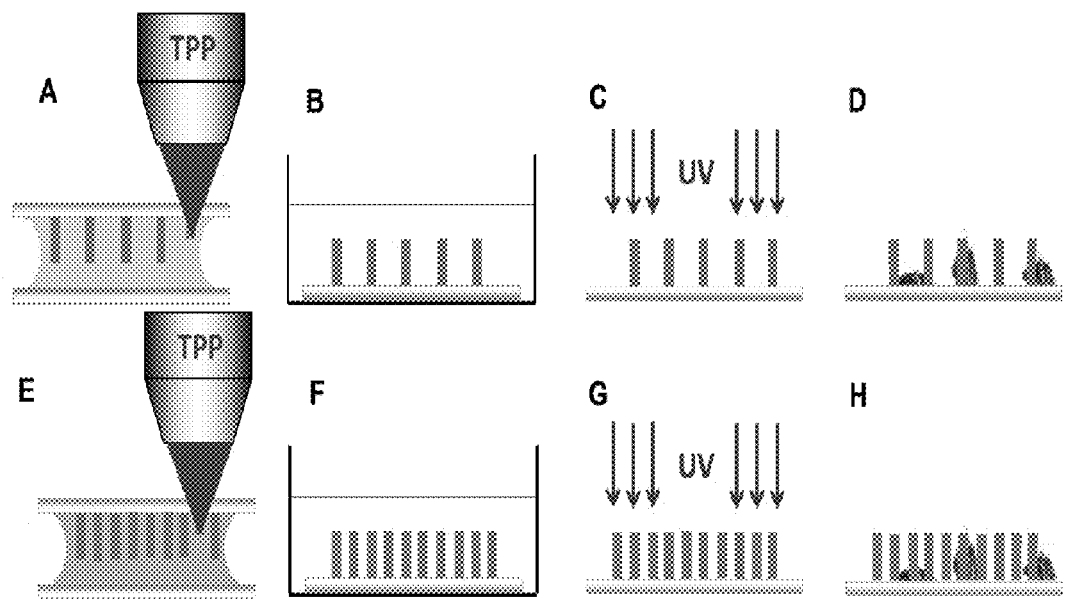
FIG. 2 shows the fabrication of microstructures using two-photon polymerization. A) By focusing a pulsed laser beam into a hybrid polymer, which is located between two cover glasses, a cross-linking reaction occurs in the area of the lens focus, and any microstructures can be generated by three-dimensional movement (here: columns arranged in a rectangular pattern). B) After structuring, the non-cross-linked parts of the resin are developed with a solvent. C) To increase the degree of cross-linking of the polymer, the structure is subjected to UV post-exposure. D) Cells are sown on the structures and their migration behavior is investigated. If differently functionalized polymers are combined within a sample, the structure is embedded in another resin after development step (B) and the structuring process (E), development in a solvent bath (F) and UV post-exposure are repeated before cells can be sown on it (H).

The quasi-3D and 3D scaffold structures were fabricated using two-photon polymerization. A pulsed femtosecond laser (Chameleon Ultra II, Coherent Inc., USA) with a wavelength of 705 nm is focused into the resin with an air lens (60×, CFI Plan Apo Lambda 0.95, Nikon, Japan) and a cross-linking reaction occurs in the area of the lens focus. The desired structures can be created by three-dimensional movement. The uncrosslinked part of the prepolymer is then dissolved in 50% isopropanol and 50% 4-methyl-2-pentanone (10 min, Sigma-Aldrich Chemie GmbH, Germany) in a development step, whereby only the crosslinked 3D scaffold structure is retained. In order to increase the degree of polymer crosslinking, the structures were finally cured using UV radiation (5 min, BK 850, Beltran®) (see FIG. 2).

In order to prepare the samples in which both polymer systems are combined, the described process step is carried out twice in succession for each polymer.

All cell migration measurements were performed with transfected *D. discoideum* cells (Dr. Günther Gerisch, Max Planck Institute of Biochemistry, Munich, Germany) expressing the green fluorescent protein (GFP) homogeneously distributed in the cytoplasm (FreeGFP).

The fluorescence images were taken with an inverted microscope (Eclipse Ti, Nikon, Japan), a 20× air lens (CFI Plan Apo 20×, Nikon, Japan) and an EMCCD camera (iXon3 897, Andor Technology Ltd., U.K.) with a resolution of 512×512 pixels. For the time lapse shots, pictures were taken every 8 seconds for 45 min.

The images were processed with the software Fiji and the autofluorescence signal of the polymer structures was removed by a reference image without cells and a binary image was generated. The Cell Evaluator software was used to determine the mass centers of gravity of the cells and thus determine the cell trajectories over time. These data were obtained by means of a Matlab algorithm of a local Mean-Squared-Displacement-Analysis (MSD-Analysis) (Arcitzet D et al. (2012) *Soft matter* 8:1473-1481; Gorelashvili M, Emmert M, Hodeck K F, Heinrich D (2014) *New J. Phys.* 16:75012; Emmert M, Witzel P, Rothenburger-Glaubitt M, Heinrich D (2017) *RSC Adv.* 7:5708-5714) in order to divide the migration behavior into directed and undirected phases and to determine the speed and other parameters (cf. FIG. 3). For this purpose, the local Mean-Squared-Displacement (MSD) ($\Delta R2(\tau)$) is calculated in an interval T around every time t depending on the delay time τ. The MSD exponent α is determined by non-linear compensation calculation with a power function:

$$\langle \Delta R^2(\tau) \rangle = \langle (R(t_i + \tau) - R(t_i))^2 \rangle_{t_i - \frac{T}{2} < t_i < t_i + \frac{T}{2}} = A\tau^\alpha$$

Figure 3:
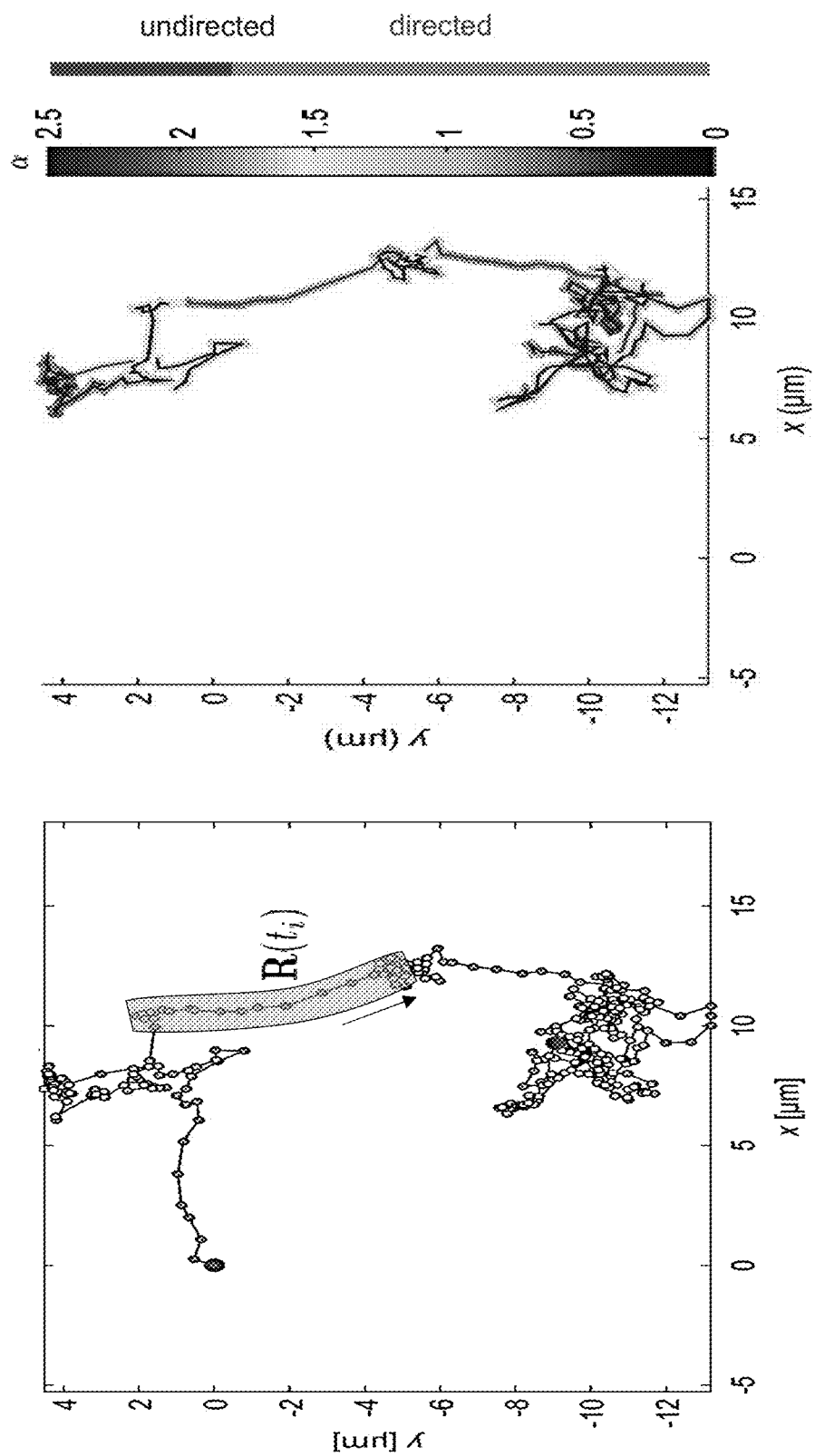
FIG. 3 shows the evaluation of the cell trajectories with local MSD analysis. To characterize the cell migration behavior, the measured cell trajectories $R(t_i)$ (left) are subjected to a local Mean-Squared-Displacement-Analysis (MSD-Analysis).
Figure 4:
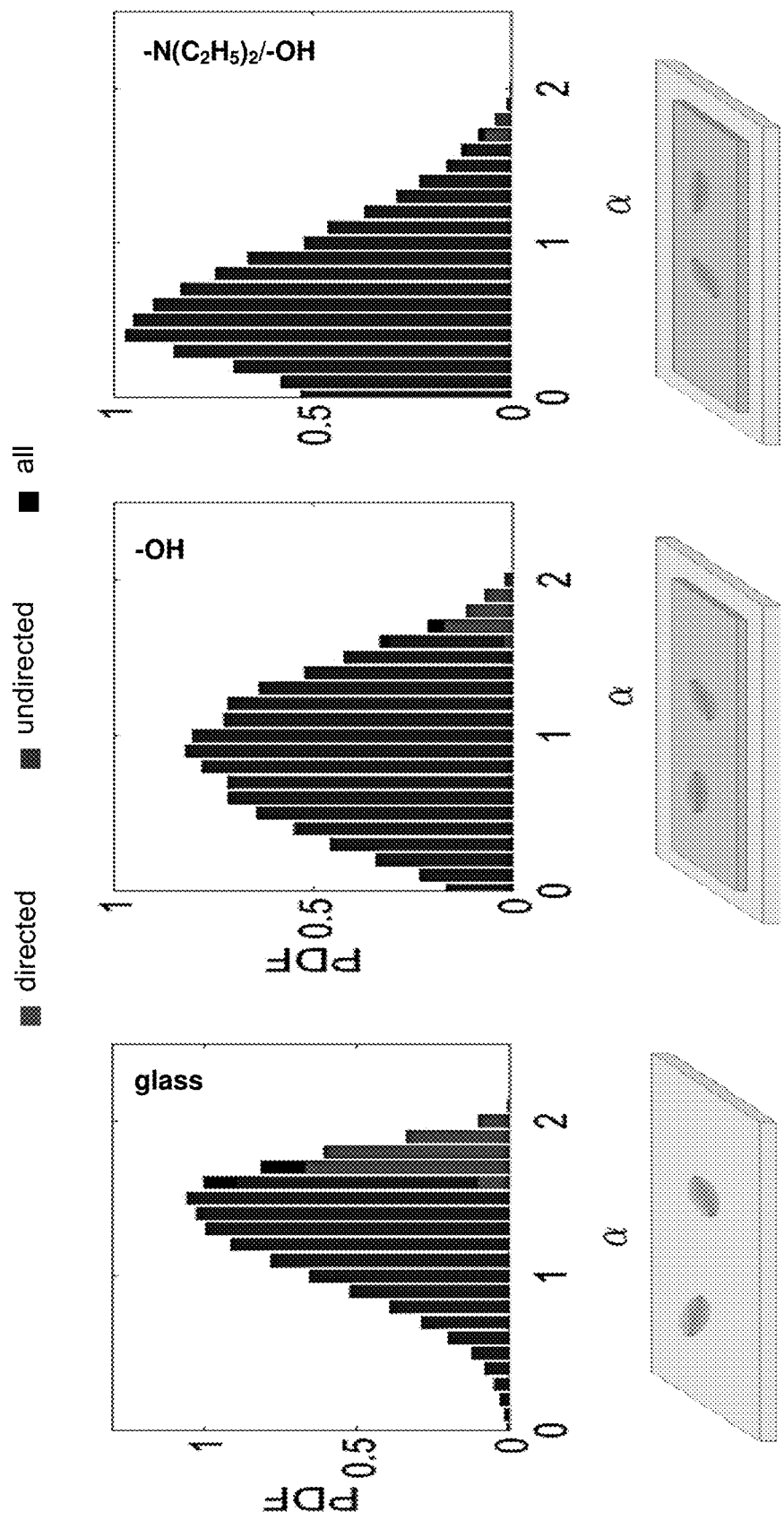
FIG. 4 shows the influence of the functionalization of polymer systems in 2D compared to glass. The distribution of the MSD exponent $\alpha$ provides information about the modes of movement of the observed cells. For $\alpha \lesssim 1.75$ the cell is in omnidirectional motion mode, for $\alpha \gtrsim 1.75$ it performs a directional motion. In comparison to glass, a clear shift to the subdiffusive range ($\alpha<1$) was observed on the polymer systems investigated. Amine/OH functionalization ($R^2$=—$N(C_2H_5)_2$/—OH) causes a significant increase in the undirected mode of motion compared to hydroxy functionalization ($R^2$=—OH).
Figure 5:
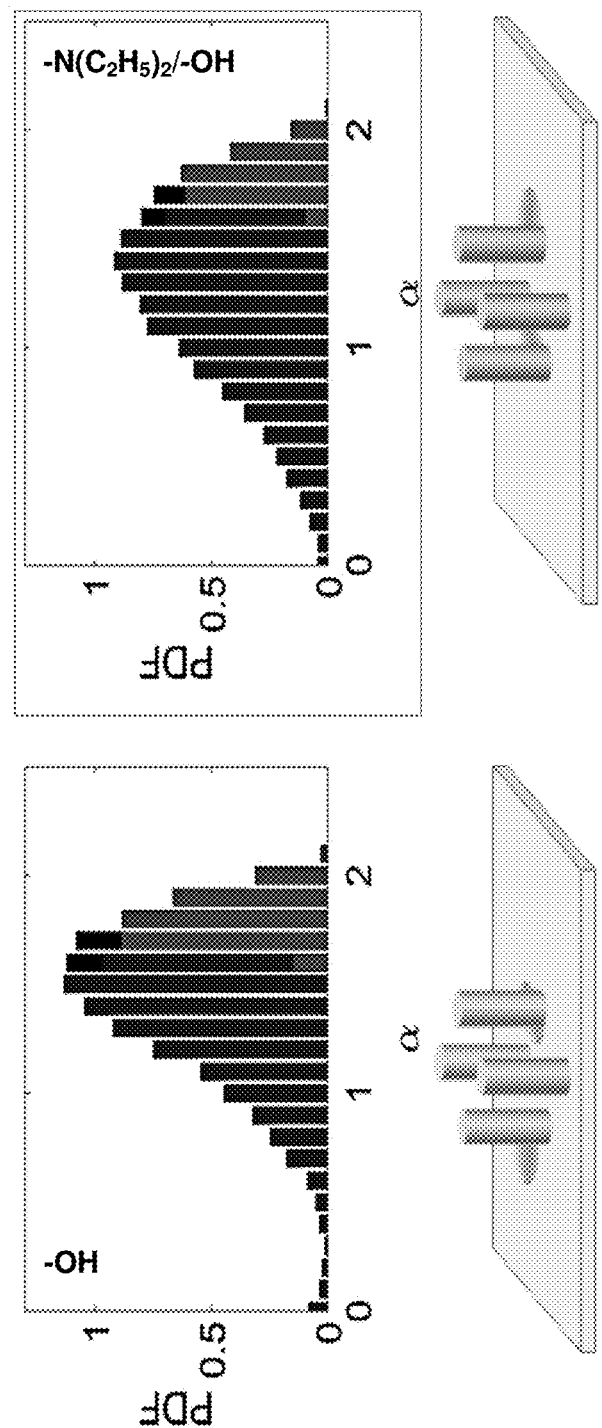
FIG. 5 shows the influence of the functionalization of polymer systems in quasi-3D. TPA-structured column fields of hydroxy- or amine-/OH-functionalized polymer system excite the directional motion mode with $\alpha>1.75$ in comparison to two-dimensional layers (FIG. 4). Again, the amine/OH-functionalized polymer system has a lower proportion of directional movements.
Figure 6:
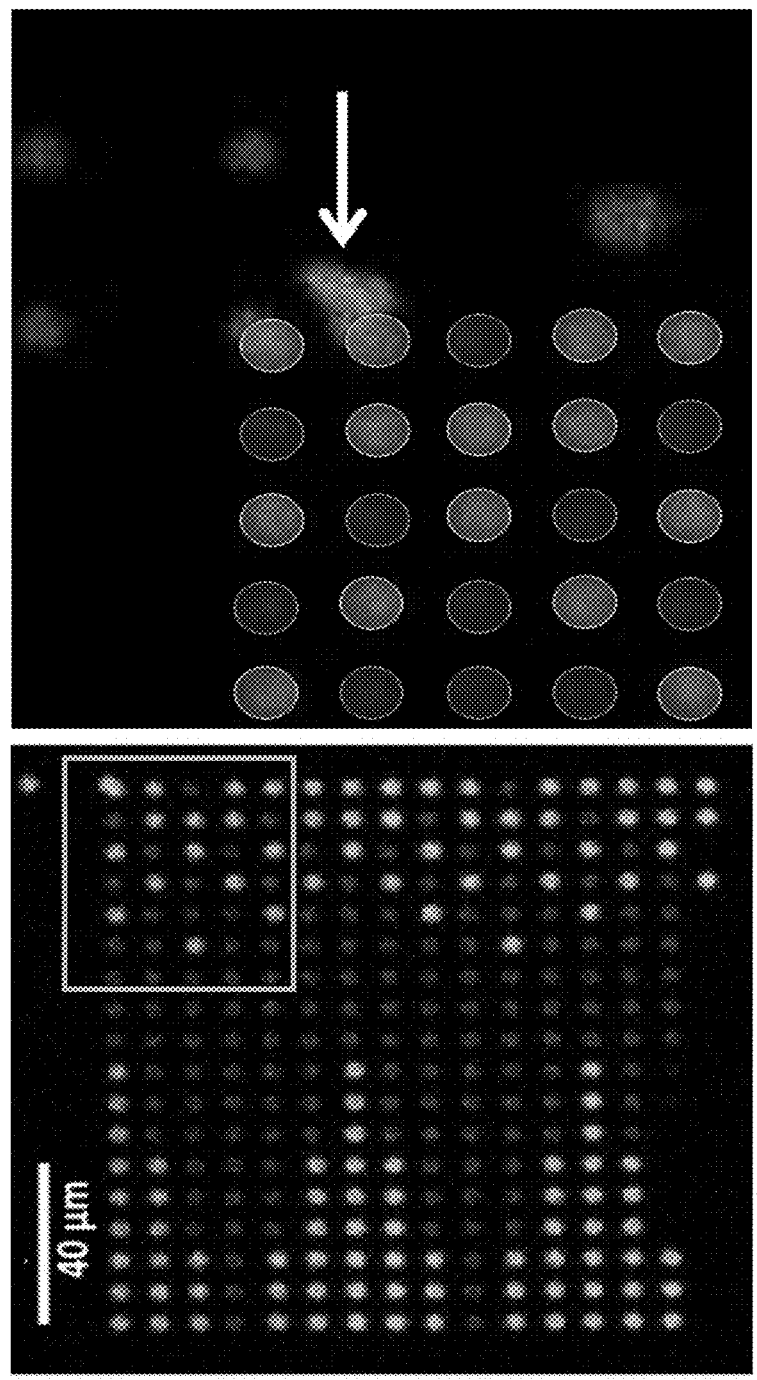
FIG. 6 shows a TPA-structured column field of OH- or amine/OH-functionalized polymer system. Left: Fluorescence microscopy image of the column field. The amine/OH-functionalized polymer system fluoresces more strongly than the OH-functionalized system. The gradient pattern on the right side of the column field allows the cells to choose between the two functionalizations at any point. Right: The marked cell of D. discoideum (arrow) shows an increased affinity to the amine-functionalized columns.
Figure 7:
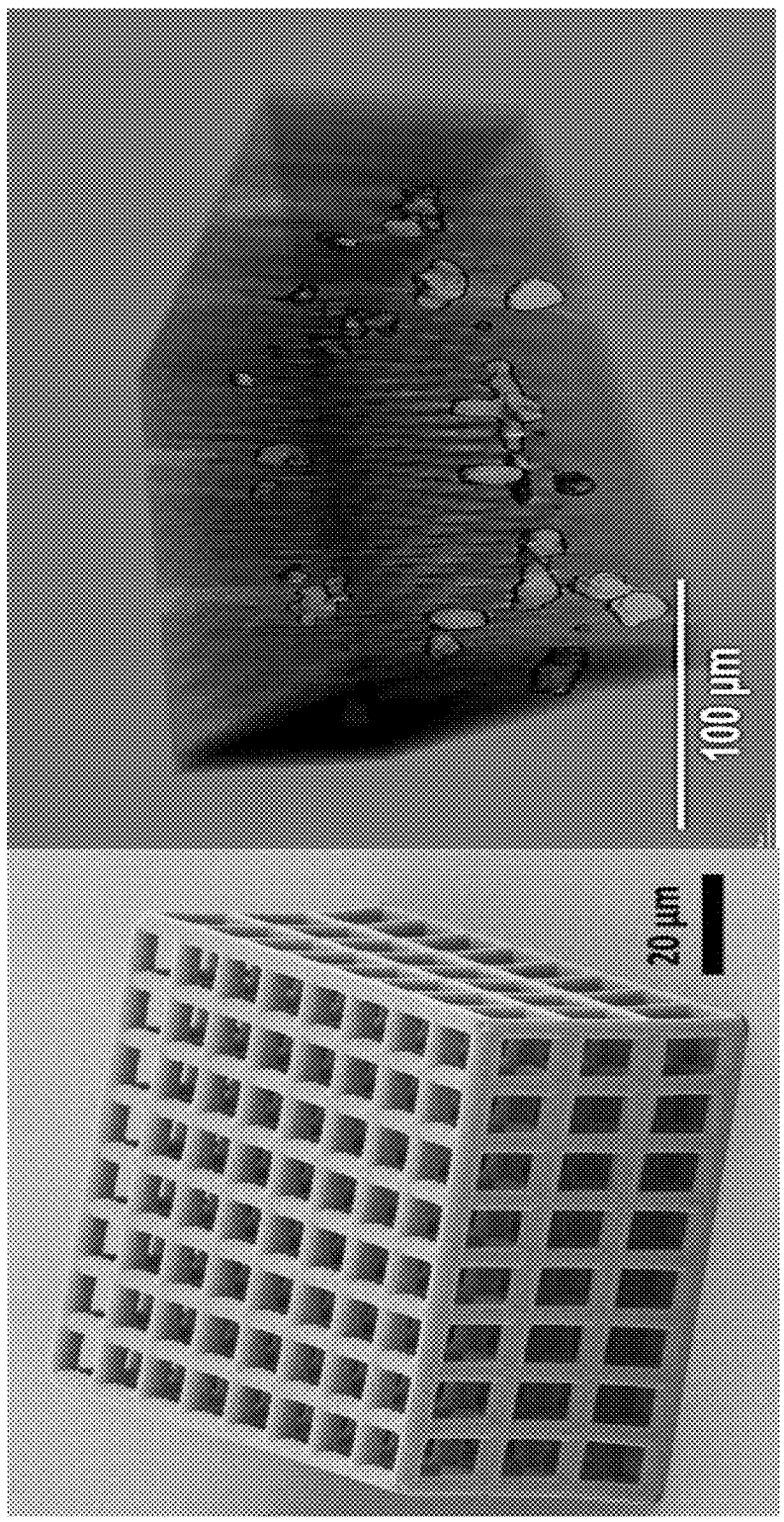
FIG. 7 shows a TPA-structured 3D scaffold structure consisting of a functionalized polymer system ($R^2$=—OH). Left: REM image of the scaffold structure. Right: Confocal fluorescence microscopy image of fluorescence-labelled cells of D. discoideum colonizing the scaffold structure.

Using the α exponent, cell trajectories can be divided into the two typical movement modes of amoeba-like cell migration (FIG. 3, right). For α≲1.75 the movement at time $t_i$ is classified as omnidirectional, for α≳1.75 the trajectory section is assigned to the directional movement mode.

Figure 8:
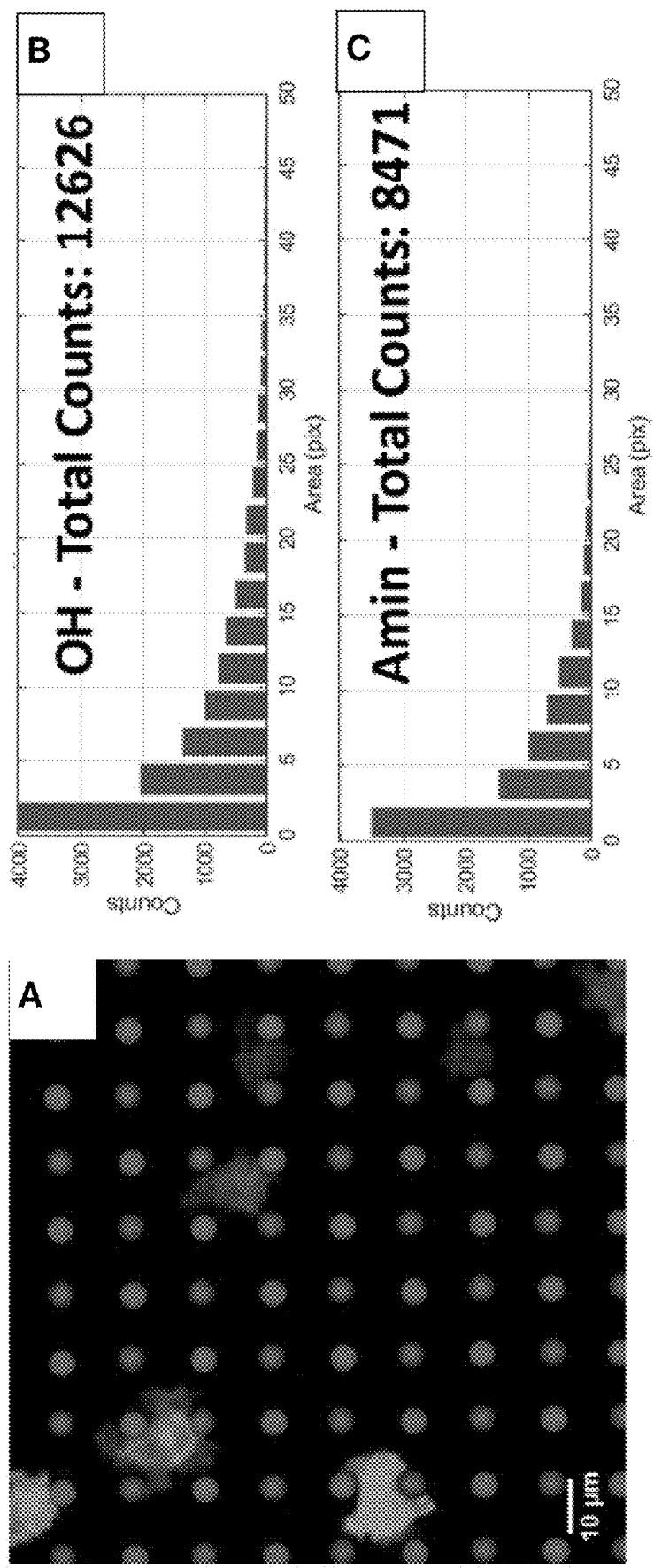
FIG. 8, part A shows a fluorescence micrograph of D. discoideum cells migrating within a field of 2PP-structured columns (height: 10 µm, diameter: 4 µm). The columns are arranged in a checkerboard pattern and consist alternately of intrinsically hydroxy-functionalized and intrinsically amine-functionalized ORMOCER®.

Application Example 3: Cell Migration Measurements in Quasi-3D Structures with Locally Different Functionalization After the influence of the three different intrinsically functionalized hybrid polymers on the cell migration behavior and the difference in 2D and quasi 3D could be shown, samples with different functionalities (—OH and —N$(C_2H_5)_2$/—OH) were prepared again. The samples were placed in a checkerboard pattern (FIG. 8A) to analyze the contact area and frequency of the cells with the structural surfaces. In FIGS. 8B and 8C, these frequencies are plotted as a function of the contact area. For the hydroxy-functionalized structures, the total number of 12626 is about 49% higher than for the amine-functionalized structures. In addition, the course of the histogram is clearly shifted towards larger contact surfaces. The cells therefore contact the hydroxystructures much more frequently, and in addition with a larger contact area. This result underscores the possibility of selectively producing chemically heterogeneous samples through intrinsic functionalization and thereby influencing cell behavior.

Influence of modulus of elasticity and surface roughness on cell behavior.

In order to exclude structural edge effects, columns with a diameter of 50 μm were structured for the modulus of elasticity measurements and their surface measured with a microindenter (Fischerscope® HM2000, Helmut Fischer GmbH). The indentation depth of 1.5 μm was reached after 20 s, followed by a relaxation time of 5 s and complete retraction within a further 20 s. The results in Table 2 show that the resulting mechanical properties do not depend on the intrinsic functionalization and therefore can not contribute to the differences in cell behavior.

TABLE 2

Different hardness parameters of 2PP-structured columns of different functionalization, determined with a microindenter.

| Functionalization | Modulus of elasticity (GPa) | Vickers hardness |
|---|---|---|
| OH | 2.31 ± 0.12 | 13.1 ± 0.5 |
| COOH | 2.28 ± 0.04 | 13.4 ± 0.7 |
| Amin | 2.34 ± 0.25 | 12.6 ± 1.5 |

Figure 9:
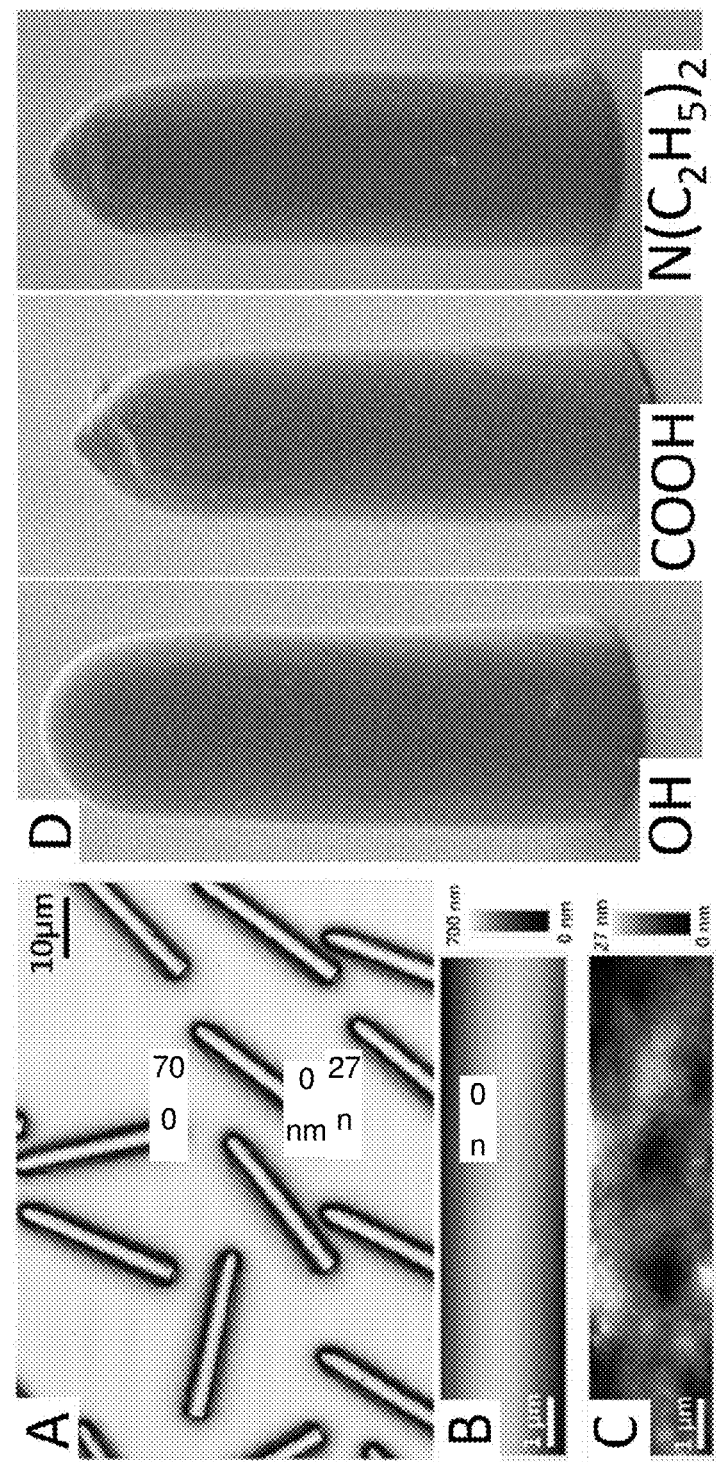
FIG. 9 shows the determination of the surface roughness of 2PP-structured columns by means of atomic force microscopy. A) Microscope image of amine-functionalized columns that have been folded down to measure the lateral surface roughness. B) Atomic force micrograph of a column. C) The surface roughness results after subtracting the surface curvature. D) Scanning electron micrographs of each column of hydroxy-, carboxy- and amine-functionalized hybrid polymer.

The surface roughness of amine-functionalized columns was determined by atomic force microscopy. The columns were folded down after structuring so that the lateral surface with which the cells were in contact during the migration experiments could be measured (FIG. 9A). A typical atomic force measurement of a column is shown in FIG. 9B, from which the surface roughness after deduction of the column curvature emerges (FIG. 9C). An average value of $R_A$= (6.8±1.6) nm results for five measured columns. The scanning electron micrographs in FIG. 9D show that there is no difference between the three materials investigated and thus no influence on cell behavior is taken. It has thus been shown that only surface functionalization leads to altered cell behavior.

Direct Detection of Functional Groups by X-Ray Photoelectron Spectroscopy:

X-ray photoelectron spectroscopy (XPS) is based on the extraction of photoelectrons by means of X-radiation from the solid to be investigated and can be used to determine the elemental composition of the sample. Since the mean free path of electrons in the solid state is very low, the information depth is a few nanometers and allows statements about the chemical composition of the surface.

Figure 10A:
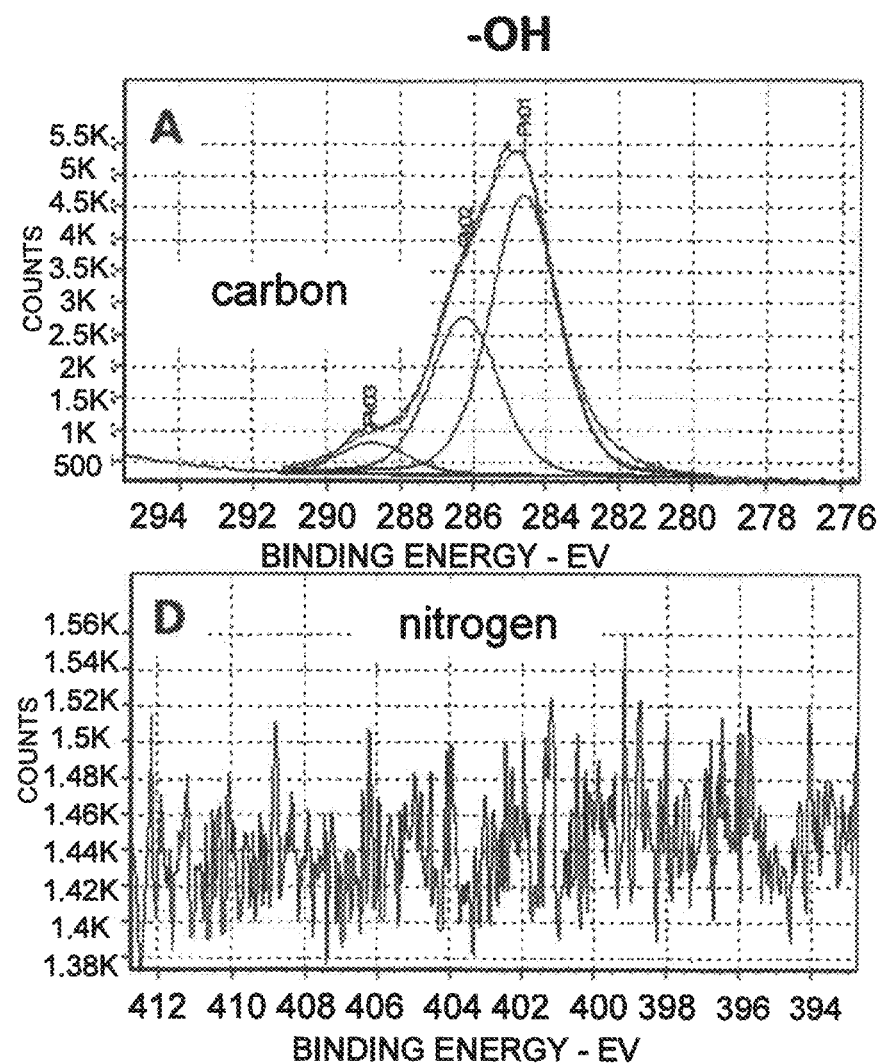
FIGS. 10A, 10B, 10C show X-ray photoelectron spectroscopy images of 2PP-structured surfaces. Shown is the carbon (1s) and nitrogen (1s) region for the hydroxy-functionalized polymer (A, D), carboxy-functionalized polymer (B, E), and amine-functionalized polymer (C, F), respectively.
Figure 10B:
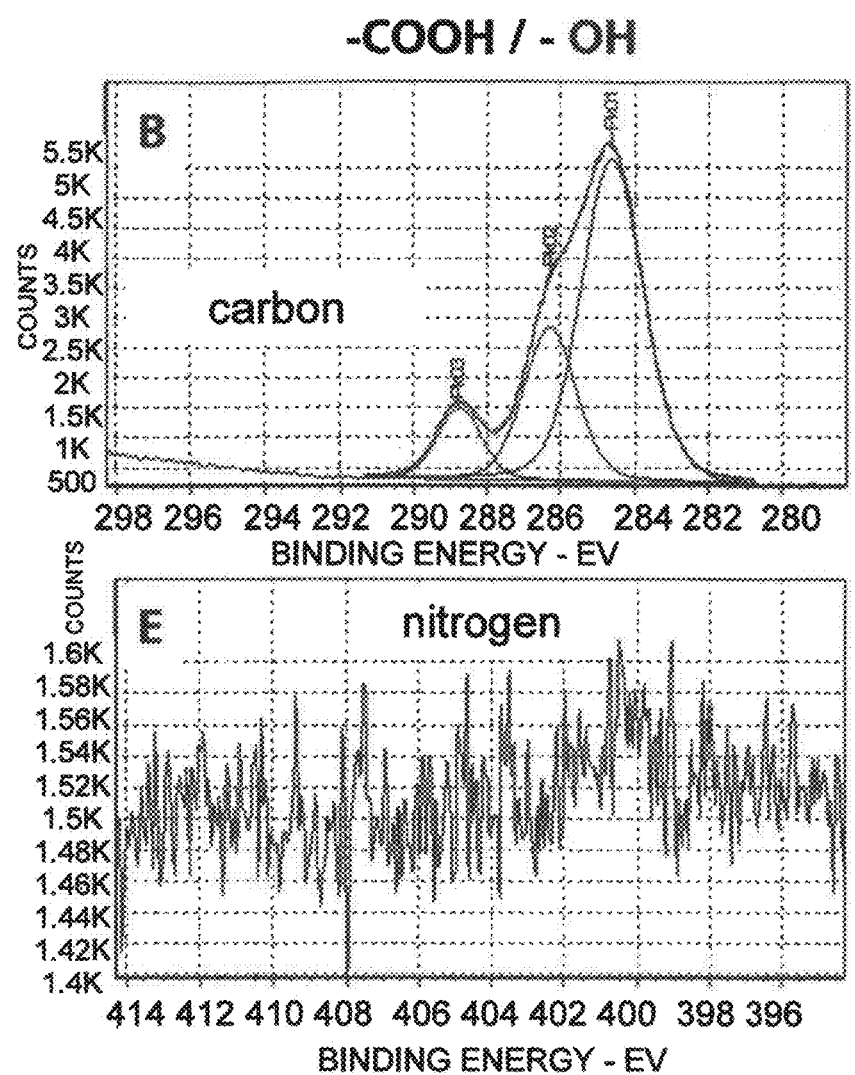
Figure 10C:
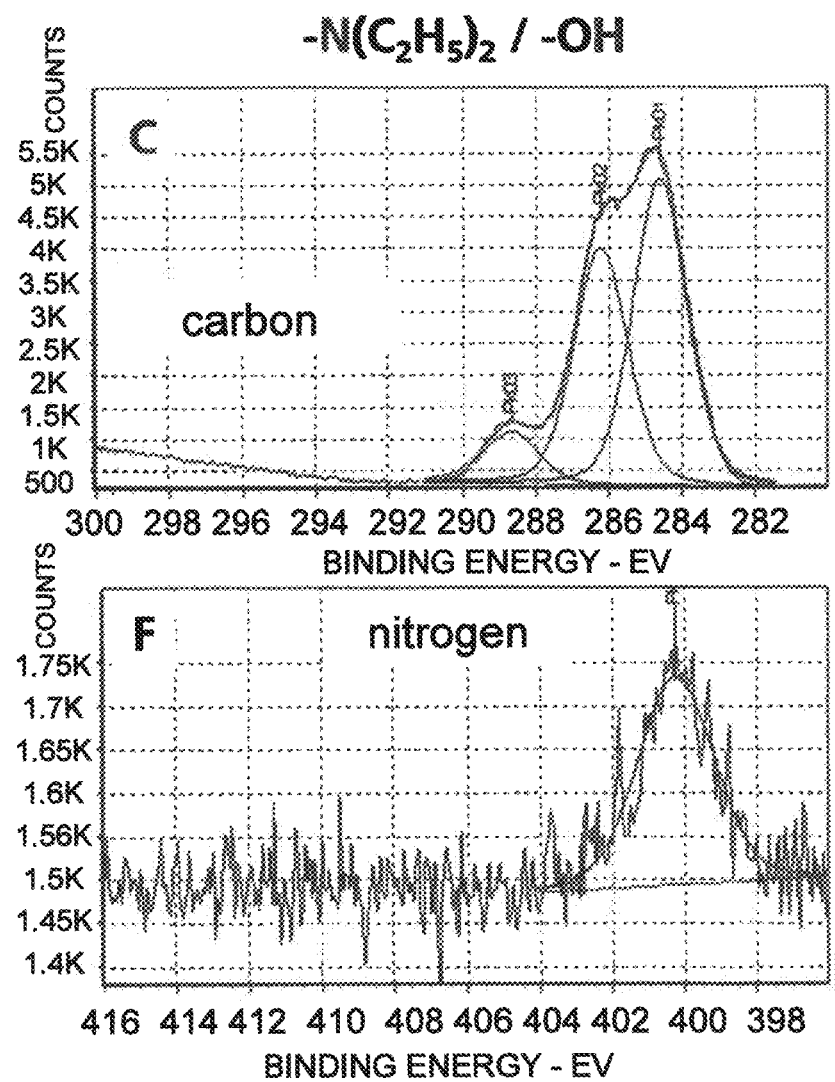

XPS was used to detect the chemical groups of intrinsic surface functionalization. For this purpose, a disk with a diameter of 5 mm was patterned by means of 2PP and investigated with an S sample from Surface Science Instruments. The evaluation was done with the software Hawk Data Analysis 7, v7.03.04. FIG. 10 shows the carbon and nitrogen regions of the 1 s orbitals of the spectrum for all three polymers investigated. In the carboxy-functionalized samples (FIG. 10B), binding energies around 289 eV are markedly more pronounced than in the hydroxy-functionalized ones (FIG. 10A), which can be assigned to carboxy groups. Carbon atoms bonded to nitrogen occur between 286-286.5 eV and lead to a corresponding increase in the spectrum in the case of the amine-functionalized sample (FIG. 10C).

Bonding energies of the 1 s orbital of nitrogen could only be detected for the amine-functionalized sample (FIG. 10F).

Since XPS is a very surface-sensitive assay, it can be assumed that both the carboxy and the amine groups on the TPA structures are accessible.

The invention claimed is:

1. A three-dimensional scaffold structure, comprising:
scaffold structure parts made of a polymer system and fluid-filled open spaces between said scaffold structure parts with a minimum extent of 50 nm in each spatial direction;
the scaffold structure configured to be filled with water as a fluid to consist of at least 50 percent by volume of water at room temperature;
said polymer system is obtained by treating a starting material with electromagnetic radiation that is locally targeted to form the scaffold structure having open spaces, said starting material containing precursor molecules of formula (I) or partially condensed species thereof:

Formula (I)

wherein the radicals and the indices have the following meaning:
B is a straight-chain or branched or cyclic organic radical having at least one C=C double bond and 4 to 100 carbon atoms;
X is hydrogen, halogen, hydroxy, alkoxy, acyloxy, alkylcarbonyl, alkoxycarbonyl or $NR^4{}_2$;
R is alkyl, alkenyl, aryl, alkylaryl or arylalkyl;
$R^2$ is OH, COOH, $NR^4{}_2$, $NR^4{}_2H^+$ or SH or a derivative thereof;
$R^4$ is hydrogen, alkyl, aryl or alkylaryl;
$R^{Rg}$ is the backbone of a straight-chain or branched hydrocarbon bonded to the Si atom, where the backbone may be interrupted by heteroatoms or heteroatom-containing groups;
a=1, 2 or 3;
b=0, 1 or 2;
a+b=3; and
c=1, 2, 3 or 4.

2. The three-dimensional scaffold structure according to claim 1, wherein the precursor molecules of formula (I) have a structure of formula (II):

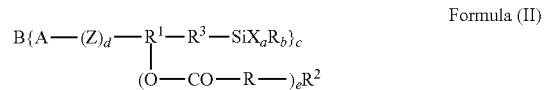

Formula (II)

wherein the radicals and indices have the following meaning:
B, X, R, $R^2$, $R^4$, a, b, a+b and c have the meaning as in formula (I);
$R^1$ and $R^3$ are, independently of one another, alkylene, arylene or alkylenearylene each having 1 to 20 carbon atoms, wherein it is possible that these radicals are interrupted by O, S, NR or NH;
A is O, S or NH for d=1 and Z=CO; or A is O, S, NH or COO for d=1;
Z is $CHR^4$; or A is O, S, NH or COO for d=0; and
e=0 or 1.

3. The three-dimensional scaffold structure according to claim 1, wherein:
said polymer system is based on at least one first type of precursor molecules of formula (I) or partially condensed species thereof and at least one second type of precursor molecules or partially condensed species thereof, wherein the second type differs from the first type at least or exclusively in that $R^2$ is hydrogen; or said polymer system is based on at least two types of precursor molecules or partially condensated species thereof which differ at least or exclusively in the group $R^2$.

4. The three-dimensional scaffold structure according to claim 3, wherein the difference is that $R^2$ is OH, COOH, $NR^4{}_2$, $NR^4{}_2H^+$ or SH in one type of precursor molecule and $R^2$ is a derivative of $R^2$ of the first type in the other type of precursor molecule.

5. The three-dimensional scaffold structure according to claim 1, wherein the derivative of $R^2$ is derived from a biofunctional molecule or from a spacer having a bound biofunctional molecule.

6. The three-dimensional scaffold structure according to claim 1, wherein the polymer system contains nanoparticles.

7. The three-dimensional scaffold structure according to claim 1, wherein said polymer systems are produced from a single type of precursor molecule, except that the precursor molecules may differ in the presence or type of derivatization at $R^2$ or in both.

8. The three-dimensional scaffold structure according to claim 1, comprising at least a first structural unit of a first thickness in a range from 10 μm to 100 mm and second structural units of a second thickness in a range from 100 nm to 1000 μm each branching off from the first structural unit, the second thickness at the branches being at most half the first thickness.

9. The three-dimensional scaffold structure according to claim 1 configured for interaction with biological cells in vitro or for medical use in vivo.

10. A method for fabricating a three-dimensional scaffold structure according to claim 1, the method comprising the steps of:

(a) providing a photostructurable source material described in claim 1,
(b) photostructuring the starting material provided in step (a) to form the three-dimensional scaffold structure; and
(c) removing unreacted starting material.

11. The method according to claim 10, which comprises performing steps (a) to (c) in a first pass with a first position of photostructuring and performing a second pass of steps (a) to (c) with a second position of photostructuring different from the first position to form two partial structures of the three-dimensional scaffold structure.

12. The method according to claim 11, wherein the starting materials of the first pass differ from the starting materials of the second pass in at least one characteristic selected from the group consisting of the type of precursor molecule of formula (I) or an inorganic polymer thereof; the proportion of the precursor molecule of formula (I) or an inorganic polymer thereof in the total photostructurable compounds; the proportion of a precursor molecule corresponding, with the exception of $R^2$=H, to the precursor molecule used of formula (I); the nanoparticle content; a proportion of the precursor molecule of formula (I) in which $R^2$ is a derivative; and a nature of the derivative of $R^2$.

13. The method according to claim 11, wherein only a single type of precursor molecule of formula (I) or an inorganic polymer thereof is used except that the precursor molecules may differ in the presence or type of derivatization at $R^2$ or in both, and wherein the type is the same or different in both passes.

* * * * *